United States Patent [19]

Suhadolnik et al.

[11] Patent Number: 5,550,111
[45] Date of Patent: Aug. 27, 1996

[54] DUAL ACTION 2',5'-OLIGOADENYLATE ANTIVIRAL DERIVATIVES AND USES THEREOF

[75] Inventors: Robert J. Suhadolnik, Roslyn, Pa.; Wolfgang Pfleiderer, Konstanz, Germany

[73] Assignee: Temple University-Of The Commonwealth System Of Higher Education, Philadelphia, Pa.

[21] Appl. No.: 333,930

[22] Filed: Nov. 3, 1994

Related U.S. Application Data

[63] Continuation of Ser. No. 849,865, Mar. 12, 1992, abandoned, which is a continuation-in-part of Ser. No. 613,848, Dec. 6, 1990, abandoned, which is a continuation-in-part of Ser. No. 204,649, Jun. 9, 1988, abandoned, which is a continuation-in-part of Ser. No. 144,602, Jan. 11, 1988, Pat. No. 4,859,768, which is a continuation of Ser. No. 629,660, Jul. 11, 1984, abandoned.

[51] Int. Cl.⁶ .......................... A61K 31/70; C07H 21/00
[52] U.S. Cl. ......................... 514/44; 514/885; 514/889; 514/934; 536/25.2; 536/25.6; 536/26.4
[58] Field of Search ........................ 536/25.2, 26.4, 536/25.6; 514/885, 889, 934, 44

[56] References Cited

U.S. PATENT DOCUMENTS

| | | | |
|---|---|---|---|
| 4,464,359 | 8/1984 | Suhadolnik et al. | 514/47 |
| 4,859,768 | 8/1989 | Suhadolnik et al. | 536/25.2 |
| 4,924,624 | 5/1990 | Suhadolnik et al. | 47/58 |
| 4,981,957 | 1/1991 | Lebleu et al. | 536/25.2 |
| 5,108,921 | 4/1992 | Low et al. | 435/240.1 |

FOREIGN PATENT DOCUMENTS

| | | |
|---|---|---|
| 0220030 | 4/1987 | European Pat. Off. . |
| WO89/12380 | 12/1989 | WIPO . |

OTHER PUBLICATIONS

Biochemistry, vol. 30, No. 8, "Cordycepin Analogues of 2',5'-Oligo-adenylate Inhibit Human Immunodeficiency Virus Infection via Inhibition of Reverse Transcriptase," Müller et al., pp. 2027-2033, (1991).

Suhadolnik et al., *The 2–5A System: Molecular and Clinical Aspects of Interferon–Related Pathway,* pp. 115–122 (1985).

FEBS Letters, vol. 158, No. 2, "3'-Omethylated analogs of 2-5A as inhibitors of virus replication," Sharma et al., pp. 298-300, (1983).

Mikhailov et al., *Helvetica Chimica Acta* 74, 887–890, (1991).

Horn et al., *Plant Physiol.* 93, 1492–1496, (1990).

Leamon et al., *Proc. Natl. Acad. Sci. USA* 88, 5572–5576, (1991).

John Goodchild, *Bioconjugate Chemistry* 1, #3, pp. 166–187, (1990).

*Primary Examiner*—James O. Wilson
*Attorney, Agent, or Firm*—Seidel, Gonda, Lavorgna & Monaco, P.C.

[57] ABSTRACT

Viral infection is inhibited in mammals by administration of metabolically stable, non-toxic 2', 5'-oligoadenylate (2-5A) derivatives that have a dual therapeutic effect. The compounds activate the intracellular latent 2-5A dependent endoribonuclease RNase L and also inhibit the action of viral DNA polymerases. Conjugates of the 2-5A derivatives for therapeutic delivery are also described.

31 Claims, 2 Drawing Sheets

DUAL ACTION 2',5'-OLIGOADENYLATE ANTIVIRAL DERIVATIVES AND USES THEREOF

CROSS-REFERENCE TO RELATED APPLICATIONS

This is a continuation of application Ser. No. 07/849,865, filed Mar. 12, 1992, which is now abandoned, which is a continuation-in-part of application Ser. No. 613,848, filed Dec. 6, 1990, now abandoned, which is a continuation-in-part of application Ser. No. 204,659, filed Jun. 9, 1988, now abandoned, which is a continuation-in-part of Ser. No. 144,602, filed Jan. 11, 1988, now U.S. Pat. No. 4,859,768, which is a continuation of application Ser. No. 629,660, filed Jul. 11, 1984, now abandoned. The disclosure of application Ser. No. 613,848 and U.S. Pat. No. 4,859,768 are incorporated herein by reference.

FIELD OF THE INVENTION

The invention relates to certain therapeutic 2', 5'-oligoadenylate analogs, pharmaceutical conjugates and compositions of such analogs, and uses thereof.

BACKGROUND OF THE INVENTION

The full nomenclature of the subject matter of the present invention involves extremely long terms. It is customary for those skilled in the art to abbreviate these terms in a manner well known to them. These general and customary abbreviations are set forth herein below and may be utilized in the text of this specification.

Abbreviations:

RT, reverse transcriptase

A, adenosine or adenylate or adenylyl cordycepin or C or 3'-dA, 3'-deoxyadenosine(3'-deoxyadenylate)

ara-A, 9-β-D-arabinofuranosyladenine

EHNA, erthyro-9-(2-hydroxy-3-nonyl)adenine

A-3'-amino, 3'-amino-3'-deoxyadenosine tubercidin, 4-amino-7(β-D-ribofuranosyl)pyrrolo-[2,3-d]pyrimidine 3'-dATP, 3'-deoxyadenosine triphosphate ATP, adenosine triphosphate I, inosine or inosinate or inosinylyl Xylo-A or xyloadenosine, 9-β-D-xylofuranosyladenine dCF or 2'-deoxycoformycin, (R)-3-(2-deoxy-β-D-erythropentofuranosyl)-3,6,7,8-tetrahydroimidazo[4,5-d][1,3]diazepine-8-ol 2-5A or 2', 5'-oligo(A) or 2', 5'-oligoadenylate, oligomer of adenylic acid with 2', 5'-phosphodiester linkages and a triphosphate at the 5'-end C, cordecypin 2', 5'-cordycepin analog or 2', 5'-oligocordycepin, oligomer of 3'-deoxyadenylic acid with 2', 5'-phosphodiester linkages and a triphosphate at the 5'-end 2', 5'-$A_n$ or core oligomer, oligomer of adenylic acid with 2', 5'-phosphodiester linkages 2', 5'-$A_3$ or 2', 5'-adenylate trimer core, adenylyl-(2', 5')adenylyl(2', 5')adenosine 2', 5'-$A_4$ or 2', 5'-adenylate tetramer core, adenylyl-(2', 5') adenylyl (2', 5') adenylyl (2', 5') adenosine 2', 5'-3'd$A_3$ or 2', 5'-C-C-C or 2', 5'-cordycepin trimer core, 3'-deoxyadenylyl (2', 5')3'-deoxyadenylyl-(2', 5')3'-deoxyadenosine 2', 5'-C-C-C-C or 2', 5'-cordycepin tetramer core, 3'-deoxyadenylyl (2', 5')3'-deoxyadenylyl (2', 5')3'-deoxyadenylyl- (2', 5')3'-deoxyadenosine 3', 5'-$A_3$, adenylyl (3', 5') adenylyl (3', 5') adenosine 2', 5'-$I_3$ or 2', 5'-inosine trimer core, inosinylyl-(2', 5')inosinylyl(2',5')inosine dd benz, benzimidazylyl(2', 5')5,6-dichlorobenzimidazole riboside, EBV, Epstein-Barr virus EBNA, Epstein-Barr virus associated early nuclear antigen HBV, hepatitis B virus HIV, human immunodeficiency virus, including HIV-1, HIV-2, and all other HIV subtypes HBLV, human B-cell lymphotropic virus HTLV, human T-cell leukemia virus, including HTLV-I, HTLV-II and HTLV-III, and all other HTLV sub-types IFNα: α-interferon rIFN-αA: recombinant α-interferon dsRNA: double-strand ribonucleic acid 2', 5'-A-A-Tu, adenylyl(2', 5')adenylyl(2', 5')tubercidin 2', 5'-Tu-Tu-Tu, 2', 5'-tubercidylyl(2', 5'1(2', 5')tubercidin 2', 5'-A-A-ara-A, adenylyl (2', 5')adenylyl (2', 5') ara-A 2', 5'-C-C-A, 3'-deoxyadenylyl (2', 5')3'deoxyadenylyl (2', 5') adenosine 2', 5'-A-C-C, adenylyl (2', 5') 3'-deoxyadenylyl-(2', 5') 3'-deoxyadenosine 2', 5'-A-A-C adenylyl (2', 5') adenylyl (2', 5')3'-deoxyadenosine 2', 5'-C-A-C, 3'-deoxyadenylyl (2', 5') adenylyl (2', 5')-3'-deoxyadenosine 2', 5'-C-C-A, 3'-deoxyadenylyl (2', 5')adenosine 2', 5'-A-C-A, adenylyl (2', 5')3'-deoxyadenylyl (2', 5')adenosine 2', 5'-xylo-$A_3$, xyloadenylyl (2', 5')xyloadenylyl-(2', 5') xyloadenosine 2', 5'-xylo-$A_4$, xyloadenylyl(2', 5') xyloadenylyl-(2', 5') xyloadenylyl (2', 5')xyloadenosine Ac, acetyl Bz, benzyl MMTr, 5'-O-p-methoxytrityl 2', 5'-trityl-$C_3$, 5'-O-p-methoxytrityl-3'-deoxyadenylyl (2', 5') 3'-deoxyadenylyl (2', 5') 3'-deoxyadenosine 2', 5'-trityl-$A_3$, 5'-O-p-methoxytrityladenylyl(2', 5')adenylyl-(2', 5')adenosine 2', 5'-C-C-dCF, 3'-deoxyadenylyl(2', 5')3'-deoxyadenylyl-(2', 5')2'-deoxycoformycin 2', 5'-A-A-A-3'-amino, adenylyl(2', 5')adenylyl-(2', 5')3'-amino-3'-deoxyadenosine SiTBD, t-butyldimethylsilyl or —Si(CH$_3$)$_2$C(CH$_3$)$_3$ 2', 5'-$A_{(Si)}$-$A_{(Si)}$-A, 3'-O-t-butyldimethylsilyladenylyl-(2', 5')3'-O-t-butyldimethylsilyladenylyl(2', 5')adenosine 2', 5'-A-A-A-3'-O-methyl, adenylyl(2', 5')adenylyl-(2', 5')3'-O-methyladenosine 2', 5'-A-A-A-3'-O-pentyl, adenylyl(2', 5')adenylyl-(2', 5')3'-O-pentyladenosine 2', 5'-A-A-A-3'-O-hexyl, adenylyl(2', 5')adenylyl-(2', 5')3'-O-hexyladenosine 2', 5'-A-A-A-3'-O-heptyl, adenylyl(2', 5')adenylyl-(2', 5')3'-O-heptyladenosine 2', 5'-EHNA-A-A, erythro-9-(2-hydroxy-3-nonyl)-adenylyl(2', 5')adenylyl(2', 5')adenosine The abbreviation for the "tetramer" compounds comprising the adenylyl (A) and 3'deoxyadenylyl (C) moieties is illustrated by the following:

2', 5'-A-A-C-C, adenylyl(2', 5')adenylyl(2', 5')3'-deoxyadenylyl(2', 5')3'-deoxyadenosine The above compounds are also abbreviated without the 2'-5' prefix, without hyphens and without the −3' suffix; hence 2'- 5'-C-C-C-3' is also abbreviated CCC.

With the expansion of the knowledge of the antiviral state induced by interferon, attention has been focused on the chemical and enzymatic synthesis and biological properties of the 2', 5'-oligoadenylates as mediators of the antiretroviral response. 2', 5'-Oligo(A) is a component of a natural, broad-spectrum antiviral defense mechanism in plants and animals. The 2-5A pathway, also known as the 2-5A/RNase L pathway or antiviral system, is widely accepted to be involved in the antiviral mechanism of interferon, and is also involved in the regulation of cell growth and differentiation.

The pathway involves the activation by 2-5A of the latent endoribonuclease, RNase L (EC 3.1.27). According to that pathway shown in FIG. 1, 2-5A is synthesized from ATP by 2', 5'-oligoadenylate synthetase [ATP: (2'- 5')oligo(A)-adenyl-transferase (EC 2.7.7.19)], hereinafter "2-5A synthetase". When activated by dsRNA, 2-5A synthetase converts ATP into 2–5A, i.e., a series of 2',5'-linked oligoadenylates characterized by a 5'-terminal triphosphate. 2-5A Synthetase exists in different isoenzyme forms, is induced by interferon, but is also detectable at lower levels in the absence of interferon. 2-5A exerts its biological effects by binding to and activating its only known target enzyme, the unique 2-5A dependent endoribonuclease RNase L. The latter cleaves viral and cellular mRNA or rRNA, thereby inhibiting protein synthesis. Hovanessian et al., *Eur. J. Biochem.* 93:515–526 (1979); Kerr et al., *Proc. Natl. Acad. Sci. USA* 75:256–260 (1978). The short half-life of the authentic 2-5A molecule in biological systems is an acknowledged disadvantage in the control of viral replication. Moreover, bioactive 2-5A is inactivated by three enzymes: a relatively unspecific 2'-phosphodiesterase, a 5'-phosphatase, and a relatively specific 2', 3'-exonuclease. Some cytokines, e.g. IL-6, activate 2-5A synthetase in such a way as to cause the enzyme or particular forms of the enzyme to produce bioinactive forms of 2-5A (Bickel, M., Dveksler, G, Dieffenbach, C., W., Ruhl, S., Midura, S., B. and Pluznik, D. H., *Cytokine* 2:238–246 (1990) and Cohen, B., Gothelf, Y., Vaiman, D., Revel, M. and Chebath, J., *Cytokine* 3:83–91 (1991)).

The 2-5A synthetase/RNase L pathway is activated following viral infection by many viruses including HIV-1 (Schröder, H. C., Wenger, R., Kuchino, Y., and Müller, W.E.G., *J. Biol. Chem.* 264, 5669 (1989); Schröder, H. C., Wenger, R., Rottman, M., and Müller, W.E.G., *Biol. Chem. Hoppe-Seyler* 369, 985 (1988)). The activation of this pathway delays the HIV infection process. To activate RNase L, the naturally occurring 2-5A molecule requires a 5'-triphosphate, which is unstable. 2-5A molecules with 5'-monophosphates or no 5'-phosphate (core) do not activate RNase L at physiological concentrations.

"Human B-lymphotropic virus" also known as "human B-cell lymphotropic virus" (HBLV), now called HHV-6, which is characterized by a large molecular weight double-stranded DNA genome is morphologically similar to viruses of the herpes virus family, but is readily distinguishable from the known human and non-human primate herpes viruses by host range, in vitro biological effects, antigenic features and genome. Salahuddin et al., *Science* 234:596–601 (1986); Josephs et al., *Science* 234:601–602 (1986). The virus has been observed to selectively infect freshly isolated human B-cells, which are converted into large, refractile mono- or binucleated cells with nuclear and cytoplasmic inclusion bodies. HBLV is suspected to be the cause of a chronic mononucleosis-like syndrome characterized by chronic fatigue lasting more than a year.

Human immunodeficiency virus ("HIV"), also known as human T-cell leukemia virus III ("HTLV-III"), the etiologic agent of acquired immune deficiency syndrome, is a type D retrovirus. As in all retroviruses, an essential feature of HIV replication is reverse transcription of the plus-strand RNA genome into DNA, a process which requires an RNA dependent DNA polymerase, reverse transcriptase. This enzyme is viral-encoded and is found associated with genomic RNA in mature HIV virions. The exclusiveness of reverse transcriptase to retroviruses and viruses requiring a short reverse transcription step makes reverse transcriptase a major target for antiviral, and particularly for antiretroviral, therapeutic intervention.

The 2-5A synthetase/RNase L system as an antiviral cellular defense mechanism has been shown to be a promising target for antiviral chemotherapy, particularly due to its interaction with double-stranded segments within viral genomes or transcripts such as the HIV-1RNA genome (Lengyel, P., *Annu. Rev. Biochem.* 51,251 (1982); Pestka, S., ed., *Methods Enzymol.* 118,119 (1986); Lengyel, P., *J. Interferon Res.* 7, 511 (1987); Sen, G. C., *Prog. Nucleic Acid Res. Molec. Biol.* 27, 105 (1982)). However, what is needed are derivatives of 2-5A which will override degradation by enzymes which inactivate authentic 2-5A. What is needed is a method for controlling HIV, chronic fatigue caused by HBLV, and other viral or cytokine-induced disease states characterized by a 2-5A pathway defect using compounds that are more metabolically stable and active than authentic 2-5A. What is needed is a method for treatment of viral infection which utilizes compounds which have broad spectrum, dual action, that is, compounds which both activate the 2-5A pathway and inhibit the activity of viral DNA polymerase.

SUMMARY OF THE INVENTION

According to one embodiment, the invention comprises the antiviral use of a novel compound of Formula I

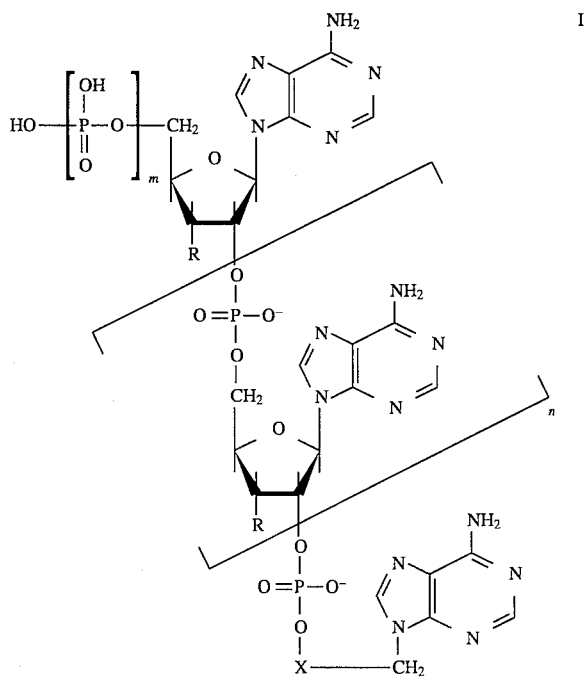

wherein
n is a whole positive integer from 1 to 8,
m is 0, 1, 2 or 3,

R is independently hydrogen or hydroxyl,

X is selected from the group consisting of C1 to C6 alkyl and C1 to C6 alkoxy, or a pharmaceutically acceptable salt thereof.

Preferably n is 1 to 3, most preferably 1 or 2.

X is preferably selected from C1 to C3 alkyl and C1 to C3 alkoxy. Compounds of Formula 1 wherein each R is hydrogen are novel.

According to another embodiment, the invention is a method of antiviral treatment comprising administering to a mammal an effective amount of one or more compounds according to Formula I, wherein n, m, R and X are defined as above, or according to Formula II

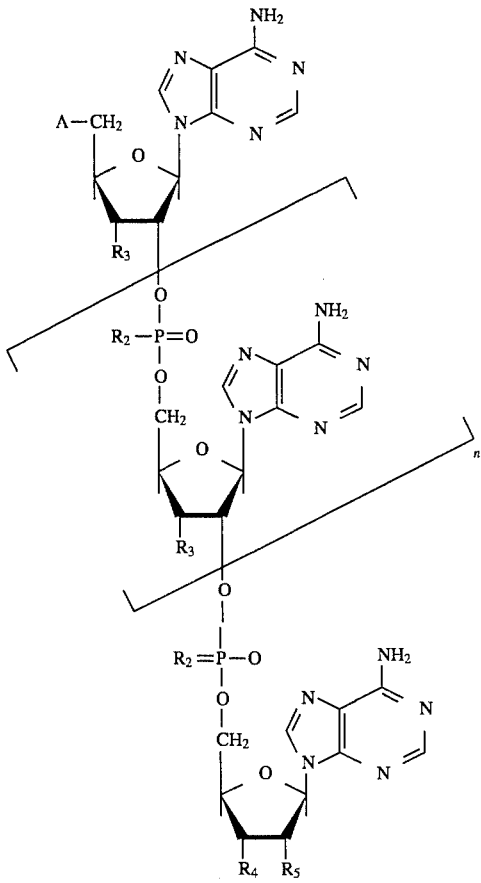

wherein
A is

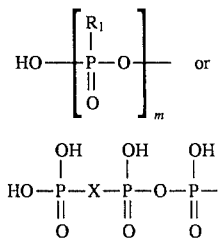

X is $NH_2$ or $CH_2$;
m is zero, 1, 2 or 3;
n is an integer from 1 to 8;
each $R_1$ is independently selected from the group consisting of oxygen, sulfur, sulfate, selenium, $C_1$ to $C_8$ alkyl and $C_1$ to $C_8$ alkoxy;

each $R_2$ is independently selected from the group consisting of oxygen, sulfur, sulfate, selenium, $C_1$ to $C_8$ alkyl and $C_1$ to $C_8$ alkoxy;

each $R_3$ is independently selected from hydrogen, hydroxyl, amino and $-OSi(CH_3)_2-C(CH_3)_3$;

$R_4$ and $R_5$ are independently selected from the group consisting of hydrogen; hydroxyl; amino; $C_1$ to $C_8$ alkyl; $C_1$ to $C_8$ alkoxy; $C_1$ to $C_8$ alkylamino, alkylcarbonyl, alkylcarboxyl and alkylhalide; and $C_1$ to $C_8$ alkoxyamino, alkoxycarbonyl, alkoxycarboxyl and alkoxyhalide;

or pharmaceutically acceptable salts thereof, excluding authentic 2', 5'-oligoadenylate and salts thereof, to simultaneously cause activation of the 2-5A synthetase/ RNase L antiviral pathway of said mammal and inhibition of viral DNA polymerase.

Preferably, n is 1 to 3, most preferably 1 or 2. According to yet another preference, the alkyl, alkoxy, substituted alkyl or substituted alkoxy groups, which may contain from one to 8 carbon atoms, preferably contain from 1 to 4 carbon atoms, most preferably from 1 to 3 carbon atoms. For halide-substituted alkyl and alkoxy groups, the halogen atom is preferably chlorine, bromine or fluorine, with chlorine being most preferred.

According to a preferred subgenus of the invention, the group A is

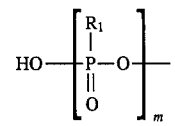

wherein m is defined above; and more preferably, at least one of $R_1$ are sulfur, where each other $R_1$ is oxygen. An additional preferred embodiment provides that at least one of $R_3$ or $R_4$ is hydrogen, the remainder being hydroxyl.

According to another embodiment, the invention is a conjugate comprising a compound according to Formula II covalently linked to an adduct which results in enhanced penetration into intact cells.

The adduct is most advantageously coupled to the oligomer through a hydroxyl oxygen at the 2' or 3' position of the 2'-terminal nucleotide, with preference being for the 2' position.

The adduct may comprise in one embodiment a vitamin selected from those vitamins which have corresponding cell receptors on targeted mammalian cells for a receptor-mediated endocytosis of the vitamin. Such vitamins useful as adducts according to the present invention include, for example, vitamin $B_{12}$, biotin, riboflavin and folic acid.

Alternatively, the adduct may comprise a lipophilic molecule or radical, such as an acyl group of the formula

wherein x is an integer from 1 to 20, preferably from 2 to 14. Another preferred lipophilic radical is cholesteryl.

According to one preferred subgenus of conjugate, the compound to which the adduct is conjugated has the structure of Formula II wherein A is

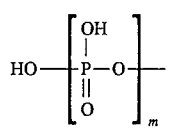

m is zero, 1, 2 or 3, n is an integer from 1 to 8, preferably 1, 2 or 3, each $R_3$ and $R_4$ is independently selected from hydrogen and hydroxyl, each $R_2$ is independently selected from sulfur and oxygen, $R_5$ is hydroxy, or a pharmaceutically acceptable salt thereof; which compound is covalently linked through the 2'-position of the 2'-terminal nucleotide thereof to the adduct.

DETAILED DESCRIPTION OF THE INVENTION

Figure 1:
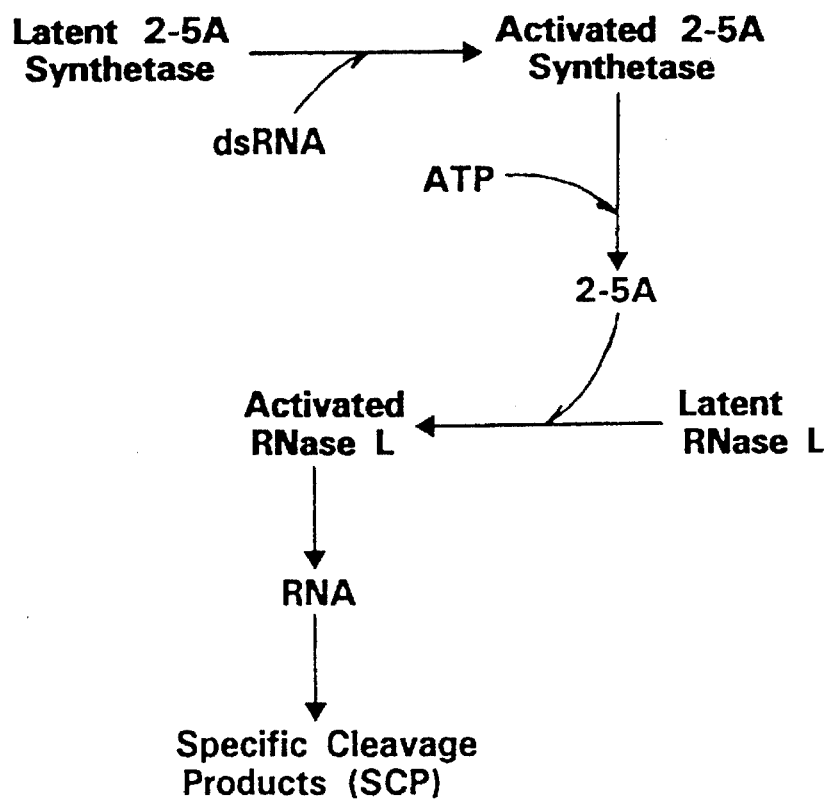
FIG. 1 is a diagram illustrating the 2-5A synthetase/Rnase L intracellular enzyme pathway.

Therapeutic agents that activate the 2-5A synthetase/RNase L antiviral defense pathway and also inhibit the activity of virally-derived DNA polymers (particularly reverse transcriptase) are used for the treatment of viral disease states. Such dual effect therapeutic agents are selective, broad spectrum inhibitors of viral DNA polymerases that are produced during viral infection. The polymerases are critical for viral replication. The compounds utilized in the practice of the invention may be characterized as derivatives of authentic 2-5A with modifications in the 5'-terminal phosphate group, ribosyl moiety and/or the internucleotide bonds. These derivatives are metabolically stable, non-toxic, and have dual antiviral effects, e.g., they activate the 2-5A synthetase/RNase L antiviral pathway and also inhibit virally-derived DNA polymerase. We have thus approached antiviral therapy by dually activating inherent antiviral mechanisms present in mammalian cells and inhibiting enzymes critical for viral information transfer.

According to one class of compounds useful in the practice of the invention, one or more of the 3'-hydroxyl groups was replaced by hydrogen atoms to form the core 2', 5'-cordycepin derivatives. This modification resulted in derivatives with increased resistance to degradation by phosphodiesterase. The preparation of such compounds is disclosed in U.S. Pat. Nos. 4,464,359 (2', 5'-oligocordycepin), and in U.S. Pat. No. 4,859,768 (2', 5'-oligocordycepin and mixed 2', 5'-oligo(cordycepin/adenosine)). The core 2', 5'-cordycepin derivatives are also non-toxic and have broad spectrum antiretroviral activity in infected cells (Montefiori, D. C. Sobol, R. W., Li, S. W., Reichenbach, N. L., Suhadolnik, R. J., Charubala, R., Pfleiderer, W., Modliszewski, A., Robinson, W. E., Jr., and Mitchell, W. M., *Proc. Natl. Acad. Sci. USA* 86, 7191 (1989); Suhadolnik, R. J., Lebleu, B., Pfleiderer, W., Charubala, R., Montefiori, D. C., Mitchell, W. M., Sobol, R. W., Li, S. W., Kariko, K., and Reichenbach, N. L., *Nucleosides & Nucleotides* 8, 987 (1989); Müller, W.E.G., Weiler, B. E., Charubala, R., Pfleiderer, W., Leserman, L., Sobol, R. W., Suhadolnik, R. J., and Schroder, H. C., *Biochemistry.*30, 2027 (1991)). Other 2-5A derivatives have been synthesized with other modifications of the 3'-hydroxyl groups, such as the substitution of amino and $OSi(CH_3)_2-C(CH_3)_3$, as described in U.S. Pat. No. 4,859, 768. Other 2-5A derivatives contain, in addition to or in lieu of 3'-hydroxyl modifications on one or more nucleotides, modifications in the 5'-terminal phosphate group. These 2-5A derivatives retain the ability to inhibit viral DNA polymerase and retain metabolic stability but, in addition, are able to activate RNase L. A variety of 2'-5'-oligoadenylate derivatives in addition to those already synthesized will exhibit enhanced antiviral activity.

According to yet another embodiment, the internucleotide phosphodiester linkage is modified. According to a preferred embodiment, sulfur is substituted for an oxygen atom to form the 2', 5'-phosphorothioate oligoadenylates. The preparation of such compounds, including optical isomers, is described in U.S. Pat. No. 4,924,624. The substitution of sulfur for oxygen in the 2', 5'-phosphodiester backbone introduceschirality into the molecules and introduces a new chemistry of the backbone. The core 2', 5'-phosphorothioates exhibit increased resistance to phosphodiesterase and phosphatases and new biological activities compared to authentic 2-5A cores. These stereochemically modified molecules are the first 2', 5'-linked core molecules able to activate RNase L. The 2', 5'-phosphorothioates act through both the activation of the 2-5A synthetase/RNase L antiviral system and the inhibition of viral DNA polymerase. The 2', 5'-phosphorothioate trimer 5'-monophosphates activate RNase L at nanomolar concentrations, similar to naturally occurring $p_3A_3$. Other molecular modifications of the internucleotide linkage provided for herein include the substitution of an oxygen atom by sulfate, selenium, C1-C8 alkyl and C1-C8 alkoxy.

In yet another embodiment, dual action, antiviral 2- 5A derivatives having increased penetration into intact cells are prepared by conjugating the oligomer to an adduct. One preferred group of adducts comprise the water-soluble vitamins (including but not limited to biotin, folic acid, vitamin $B_{12}$, or riboflavin). Other preferred adducts include lipophilic molecular and chemical groups such as, for example, acyl or cholesteryl groups. Such conjugates are internalized by intact cells by exploiting receptor-mediated endocytosis.

Administration of exogenous, metabolically stable, dual action analogs of 2-5A will render increased protection against disorders characterized by a 2-5A defect, particularly protection against viral infection in animals and humans. By "2-5A defect" as used herein is meant any manifestation, condition or interruption of the 2-5A pathway which results in a physiologically consequential change in the production of authentic 2-5A, and/or the interruption of 2-5A-dependent activation of RNase L. Afflictions characterized by a 2-5A defect include, for example, viral infections, particularly HTLV infection, most particularly HIV infection, chronic fatigue and other HHV-6 related disorders, hepatitis B and other infections of the hepatitis virus family, cutaneous T-cell lymphoma and other HTLV-1 related disorders, etc. Other diseases that are relevant include chronic myelogenous leukemia; acute leukemia; cancer; T-cell leukemia;

Alzheimer's disease; Parkinson's disease; multiple sclerosis; autoimmune disease; and surgery- and other trauma-induced immune dysfunction. 2-5A pathway defects are particularly manifested in diseases characterized by both chronic viral infection and immune cell defects.

Structural modification of the 2-5A molecule at the 3'-hydroxyl groups and elsewhere provides 2-5A analogues with remarkably increased metabolic stability to 2'-phosphodiesterases and cellular nucleuses, while maintaining the ability to activate RNase L and inhibit retroviral reverse transcriptase. Likewise modification of native 2-5A by substitution of the 3'-terminal nucleotide results in a more stable molecule. Persistent, high intracellular concentration of the metabolically stable 2-5A analogs are a consequence of their increased stability. Additionally, modifications of the 5'-terminal enhance the ability of the 2-5A molecule to activate RNase L.

The longer-lasting pharmacological activity of the 2-5A analogs offer a more favorable therapeutic ratio. This allows a decreased frequency of administration relative to 2-5A, which is metabolically unstable. Decreased frequency of administration is important due to the chronic nature of many afflictions characterized by 2-5A pathway defects. In addition, certain modifications of 2-5A derivatives that facilitate penetration into the cell further increase the therapeutic ratio by reducing the amount of the derivative that must be administered to give a therapeutic effect.

The 2-5A analogs are particularly useful in the treatment of infections caused by viruses. The 2-5A pathway defect associated with viral infection comprises the inactivation of the pathway caused by the virus' interference with the activation of 2-5A synthetase by dsRNA. In the absence of 2-5A synthetase activation, 2-5A production, and hence activation of RNase L, is reduced. According to the present invention, exogenous, metabolically stable 2-5A analog is administered to counteract this virally-caused defect in the 2-5A pathway. The 2-5A analogs, like authentic 2-5A, are capable of activating RNase L, which cleaves viral RNA.

The 2-5A analogs are particularly useful in protecting against infection by the various human T-cell leukemia viruses (collectively "HTLV"), such as HTLV-I, which cause cutaneous T-cell lymphoma; HTLV-II, which causes Sezany lymphoma: HTLV-III; and HTLV-IV, which is presently believed to be the etiologic agent of multiple sclerosis. Each of the HTLV viruses is a retrovirus Also known as "HIV-1", HTLV-III is responsible for causing acquired immune deficiency syndrome ("AIDS"). The compounds are further believed useful in treating HIV-2, a second serologically distinct HIV subtype. Hereinafter (HIV) shall mean either HIV-1 or HIV-2, and any other HIV subtypes now or hereinafter known.

The 2-5A analogues are also particularly useful in protecting against infection by the various hepatitis viruses which cause viral hepatitis. The hepatitis B virus, in particular, is thought to be a composite of a retrovirus and a virus that employs replication of a DNA genome by DNA dependent DNA polymerase. The 2-5A analogues are also particularly useful in protecting against infection by viruses with a DNA genome, such as herpes viruses.

HTLV-infected patients, in particular HIV-1-infected patients, have been shown to demonstrate unusually low levels of 2-5A and/or RNase L activity in blood mononuclear cells. Blood mononuclear cells from healthy individuals, by contrast, display higher 2-5A levels, on average, and RNase L activity is readily detectable. Likewise blood mononuclear cells of chronic fatigue-inflicted individuals exhibit low 2-5A levels, and evidence the appearance of novel RNA cleavage products, distinct from the specific cleavage products observed in blood mononuclear cells from normal individuals.

While the practice of the invention is illustrated herein with regard to the treatment of HIV-1 infection, which is generally regarded as a prototypical retrovirus and HbV infection, which has properties both of retroviruses and DNA genome viruses, the method of the invention has application to the treatment of any diseases wherein the etiologic agent comprises a virus.

In addition, chronic virus infections are commonly associated with cytokine imbalances that produce additional pathogenic effects, including the accumulation of bioinactive 2-5A. The present invention operates to correct the effects of this imbalance by supplying bioactive 2-5A.

The preparation of certain of the compounds utilized in the practice of the present invention are described in U.S. Pat. Nos. 4,859,768 and 4,924,624. The other compounds used in the practice of the invention may be prepared by following the general synthetic techniques described in those patents.

Examples of compounds for use in the method of the invention include the following core compounds, their corresponding 5' mono-, di-, and triphosphates, and the pharmaceutically acceptable salts of any of them:

Mixed cordycepin/adenosine oligomers

2', 5'-C-C-C,
2', 5'-A-A-C,
2', 5'-A-C-C,
2', 5'-C-C-A,
2', 5'-C-A-C,
2', 5'-C-C-A, and
2', 5'-A-C-A, in addition to the various "tetramer" combinations of A and C, including but not limited to,
2', 5'-C-C-C-C,
2', 5'-A-A-A-C,
2', 5'-A-A-C-C,
2', 5'-A-A-C-A, and the like.

Alkoxy compounds

2', 5'-A-A-A-3'-O-methyl
2', 5'-A-A-A-3'-O-pentyl
2', 5'-A-A-A-3'-O-hexyl
2', 5'-A-A-A-3'-O-heptyl Amino compounds 2', 5'-A-A-A-3'-amino Miscellaneous compounds 2', 5'-A(Si)A(Si)A
2', 5'-A-A-ara-A,
2', 5'-A-A-Tu,
2', 5'-Tu-Tu-Tu,
2', 5'-$I_3$,
2', 5'-xylo-$A_3$,
2', 5'-xylo-$A_4$,
2', 5'-C-C-dCF,
2', 5'-EHNA-A-A, and 5,6-dichlorobenz imidazylyl (2',5') 5,6-dichloro-benzimidazylyl (2',5') 5,6-dichlorobenzimidazole riboside, 3'-deoxyadenylyl-(2'-5')-3'-deoxyadenylyl-(2'-4')-9-(4'hydroxybutyl)adenine, and 3'-deoxyadenylyl-(2'-5')-3'-deoxyadenylyl-(2'-4')-9-(4'hydroxyethoxy) adenine.

The two last mentioned compounds, characterized by an ether linkage between a cordycepin nucleotide and adonine, are from a group collectively referred to as "C-C-ether-A". Correspondingly, when the cordeycepin residues are substituted by adenosine, the compounds are referred to collectively as "A-A-ether-A". Hereinafter, the particular A-A-ether-A compound wherein the ether linkage comprises —$CH_2CH_2OCH$— is referred to as "A-A-$CH_2CH_2OCH_2$-A". The complete chemical name is adenylyl-(2',5')-adenylyl-(2',2')-9-[(2"hydroxethoxy) methyl]adenine.

Inhibition of HBV Replication by 2-5A Derivatives

The antiviral activity of several 2-5A derivatives against hepatitis B virus was tested. Human liver cells chronically producing HBV (Acs et al., *Proceedings of the National Academy of Sciences, USA* 84:4641–4645 (1987)) were seeded into 24 well tissue culture plates and grown to confluence. 2-5A derivatives were then added at 20 µM for a continuous 9 day period. Culture medium was changed daily. Spent culture medium was analyzed for extracellular HBV DNA after 0, 3, 6 and 9 days. Treated cells were lysed 24 hours following the 9 day treatment and analyzed for intracellular genomic DNA forms. The protocol has been published by Korba and Milman (*Antiviral Research* 217:217 (1991)). The assay parameters are described in more detail below.

Both intracellular and extracellular HBV DNA were analyzed by procedures that are routine in the art in order to (1) allow for verification of compound efficacy, and (2) provide possible data on the target site in the HBV replication pathway for the compound from the examination of the pattern of viral replicative forms. The culture medium was changed daily during the treatment period to (1) prevent the buildup of potentially toxic metabolites from the test compounds, and (2) provide an analysis of HBV virion production during discrete 24-hour intervals which enables a quantitative comparison of any effect on virion production.

The analysis of HBV DNA was performed using blot hybridization techniques (Southern and slot blot) and [$^{32}$P]-labeled HBV-specific probes. HBV DNA levels were measure by comparison to known amounts of HBV DNA standards applied to every nitrocellulose membrane (gel or slot blot). An AMBIS beta scanner, which measures the radioactive decay of the hybridized probes directly from the nitrocellulose membranes, was used for the quantitative analysis. Standard curves, generated by multiple analyses, were used to correlate cpm measurements made by the beta scanner with relative levels of target DNA. The levels of HBV virion DNA released into the culture medium were analyzed by a slot blot hybridization procedure. HBV DNA levels were then compared to those at day 0 to determine the effect of drug treatment.

The levels of replicate intermediate and episomal monomers were used as an indicator of the relative levels of HBV replication. Integrated HBV DNA was used to normalize the relative amounts of DNA in each lane because the levels of this class of HBV DNA remain constant on a per cell basis. Inhibition of HBV DNA replication is indicated by the loss of replicative intermediates without changes in the level of integrated HBV DNA. In this assay, the following 2-5A derivatives showed anti HBV activity: xyloA$_3$, A-A-$CH_2CH_2OCH_2$A, EHNA AA, CAC, ACCA and dd benz.

To study these inhibitions further, 5 of those 2-5A derivatives were diluted and tested at 2 µM and 6 µM, in addition to 20 µM. The five 2-5A derivatives displayed marked anti-HBV inhibitory power at 20 µM and 3 of the 5 (A-A-ether-A, dd benz and CAC) were also very active at 2 µM. These results demonstrate that a variety of 2-5A derivatives are active against HBV. In accordance with the invention, the inventors conclude that anti HBV of these and other 2-5A derivatives will be enhanced by adding 5' terminal modifications that augment the ability of the 2-5A derivatives to activate RNase L. Also in accordance with the invention, the inventors conclude that anti HBV activity will be augmented further by conjugating said 5' modified and 5' unmodified 2-5A derivatives with lipophyllic adducts such as cholesterol, palmitate, folate, etc.

To determine the therapeutic ratio of the 5 2-5A derivatives that were titrated for anti-HBV activity, their toxicity was measured with a conventional neutral red assay. The protocol for determining the toxicity of these compounds in culture is routine in the art and can be summarized as follows. 2.2.15 cells were grown to confluence in 96 well flat-bottom tissue culture plates and treated with compounds in 0.2 ml of culture medium per well. Four concentrations of each compound were assayed, each in triplicate cultures. Untreated control cultures were maintained on each 96 well plate. On each 96 well plate, wells containing no cells were used to correct for light scattering. Toxicity was determined by the inhibition of uptake of neutral red dye, as determined by the absorbance at 510 nanometers relative to untreated cells (Finter et al., *J. Med. Chem* 5:419 (1969)), 24 hours following day 9 of treatment.

No toxicity was observed for the aforesaid 2-5A derivatives at the highest concentration tested for antiviral activity (20 µM). Of the five 2-5A derivatives tested, four showed no toxicity at 9 times the effective antiviral dose (180 µM) and the fifth, dd benz, showed low toxicity at 180 µM.

To study further the specificity of the HBV inhibition by the said 2-5A derivatives, their breakdown products were tested for possible anti HBV activity. No anti HBV activity was found with benzimidazole, dibenzimidazole$_2$, adenosine, cordecypin or 9-β-D-xylofuranosyladenine. These results show that the said 2-5A derivatives specifically inhibit the replication of HBV at concentrations that are not toxic to uninfected cells and that the inhibition is due to the 2-5A derivatives and not to their metabolites.

Viral Inhibition by Phosphorothioate Oligomers

RNase L is a key functional enzyme of the 2-5A synthetase/RNase L antiviral defense pathway. The activation of this unique 2-5A-dependent endoribonuclease by 2-5A derivatives and the subsequent hydrolysis of viral RNA is critical in the inhibition of virus replication and regulation of cell growth. Some of the antiretroviral properties of interferon are mediated by activation of the 2-5A synthetase/RNase L pathway. Direct activation of RNase L by 2-5A derivatives bypasses the requirement for interferon in establishing an antiretroviral state. Modification of the 2-5A molecule at the 3'-hydroxyl groups and the 2', 5'-internucleotide linkages has resulted in 2-5A derivatives that are metabolically stable (and therefore resistant to degradation by phosphodiesterases and phosphatases) and biologically active (capable of activating RNase L). Manipulation of synthetic procedures permits the design and synthesis of 2-5A derivatives which (i) display increased metabolic stability against nucleolytic degradation, (ii) are phosphatase-resistant, (iii) do not require 5'-phosphorylation for activation of RNase L, and (iv) can be transported into intact cells. Chirality was introduced into the 2', 5'-phosphodiester bond of the 2-5A molecule as an approach to differentiate between RNase L activation and inhibition at the molecular level. The pure dimers and trimers of the diastereomeric phosphorothioate derivatives of 2-5A were first synthesized enzymatically. More recently, chemical synthesis, purification and identification of the two dimer, four trimer and eight tetramer diastereomers have been achieved via the phosphotriester and phosphoramidite approach. These chiral molecules exhibit striking biological activities which altered the dogma that three adenylate residues and two 5'-terminal phosphates were required to activate RNase L. In contrast to authentic 2-5A core molecules which are unable to activate RNase L, three of the four 2', 5'-phosphorothioate trimer cores (RpRp, SpRp and RpSp) bind to and activate RNase L (at $10^{-5}$M), as do the 2', 5'-phosphorothioate 5'-monophosphates (pRpRp, pRpSp, and pSpRp) (at $10^{-8}$M).

To determine whether these in vitro studies could be extended to an in vivo model with virus-infected cells, the 2', 5'-phosphorothioate tetramer 5'-monophosphates were microinjected into the cytoplasm of HeLa cells and the cells were then challenged with VSV. The 2', 5'-phosphorothioate tetramer 5'-monophosphates (pRpRpRp, pSpRpRp and pRpSpSp) all activated RNase L. However, the pSpSpSp isomer (at concentrations as high as $10^{-6}$M) did not. Microinjection of the pSpSpSp inhibitor simultaneously with 2-5A eliminated protection against VSV replication The $R_p$- and $S_p$-2', 5'-phosphorothioates inhibit HIV-1 replication in intact cells in culture. The 2', 5'-phosphorothioates protect target cells from HIV-1 infection by inhibition of HIV-1 RT (measured in Triton X-100-activated lysates of HIV-1 virions from H9/HTLV-IIIB culture supernatants). HIV-1 RT was not inhibited by $A_3$ or $p_3A_3$ at 0.25–256 μM. In contrast to 2-5A, the 2', 5'-phosphorothioate tetramer 5'-monophosphate derivatives are very effective inhibitors of HIV-1 RT activity. The most effective inhibitor of HIV-1 RT in HIV-1-infected cell lysates is $p_3A_3$ αS with 50% inhibition observed at 0.5 μM. AMPS did not inhibit HIV-1 RT up to 200 μM, suggesting that degradation products are not responsible for the inhibition observed with 2', 5'-phosphorothioates.

d $(T)_{16}$ and tRNA$^{Lys.3}$ bind specifically to the kinetically significant primer binding site of homogeneously pure recombinant p66 HIV-1 RT as demonstrated in UV crosslinking studies. Binding of oligo d$(T)_n$ to p66 RT is not affected by dNTPs; in competition assays, the primer analogs, Sd$(C)_{28}$ and d$(C)_{19-24}$, the natural primer tRNA$^{Lys.3}$ and $p_3A_3$αS inhibit oligo d$(T)_n$-p66/RT complex formation in a first-order exponential manner. The inhibition of HIV-1 RT by 2-5A and 2-5A derivatives occurs at the primer binding site. Under equilibrium binding conditions, 2', 5'-$p_3A_4$ exhibits first order binding kinetics with one half competition at 55 μM ($K_D$=31×$10^{-6}$M). 2', 5'-$p_3A_4$αS exhibits first order binding kinetics with one half competition at 5.1×$10^{-6}$M ($K_D$=2.9×$10^{-6}$M). 2',5'-$A_3$ core, 2', 5'-p$A_3$, 3'5'-$A_3$ core, 3', 5'-p$A_3$, 3', 5'-$p_3A_3$ and ATP do not inhibit binding of HIV-1 RT to d$(T)_{16}$.

The 2', 5'-cordycepin trimer core and 5'-monophosphate (1 μM) (when incorporated into anti-body-targeted liposomes specific for the T cell receptor molecule CD3) inhibited 90% of HIV-1 replication. See Table 1 of Müller, W.E.G., Weiler, B. E., Charubala, R., Pfleiderer, W., Leserman, L., Sobol, R. W., Suhadolnik, R. J., and Schröder, H. C., *Biochemistry* 30., 2027 (1991). Dot-blot and gel-retardation assays showed that 2', 5'-cordycepin trimer core and 5'-monophosphate interfere with the binding of tRNA$^{Lys.3}$ to HIV-1 RT. See FIG. 3 of Müller et al. The aforesaid publication is incorporated herein by reference. p$C_3$ did not stimulate RNase L activity and displayed no effect on the amount of cellular RNA or protein. At a concentration of 10 μM, the cellular DNA polymerases α, β and γ were almost insensitive to $C_3$ or p$C_3$ [Co=cordycepin].

We have available for the first time, antiretroviral molecules (2-5A derivatives) which possess dual effects on HIV-1-infected cells: (i) they activate the 2-5A synthetase/RNase L antiretroviral system and (ii) inhibit HIV-1 RT. With the 2', 5' -phosphorothioate cores and their 5' -monophosphates, it is possible to prevent acute infection (by inhibition of HIV-1 RT) and simultaneously degrade HIV-1 mRNA by activation of RNase L.

Conjugates of 2,5'-Oligoadenylate Derivatives Having Increased Cellular Uptake

To facilitate internalization of 2-5A derivatives into intact cells, bioactive 2-5A derivatives are conjugated to water-soluble vitamins (folic acid, biotin, riboflavin, or vitamin $B_{12}$) or to lipophilic chemical groups. By exploiting this technique, 2-5A derivatives may be delivered to intact cells without membrane damage. This approach involves (i) the synthesis of bioactive, metabolically stable derivatives, e.g., 2', 5'-$C_n$, 2', 5'-phosphorothioates (prepared according to U.S. Pat. No. 4,924,624), and other metabolically stable derivatives such as those disclosed in U.S. Pat. No. 4,859, 768 and co-pending application Ser. No. 613,848. 2-5A derivatives according to the disclosure of the above-mentioned documents, have been designed, synthesized and tested for their antiretroviral effect at the level of RNase L and inhibition of RT 2', 5'-Oligonucleotides may be prepared enzymatically in multistep chemical syntheses via the phosphotriester and phosphoramidite approach, in milligram and gram amounts, respectively. The correct choice of appropriate blocking groups for sugar, base and phosphate protection determines yields, ease of purification and chromatographic behavior.

The successful facilitated delivery of biologically active, metabolically stable 2-5A derivatives is key to continuation of the mechanistic studies of inhibition of HIV-1 replication, and effective drug delivery. Several strategies for the assisted delivery of 2-5A derivatives into intact cells may be used.

2', 5', Oligoadenylate Lipophilic Conjugates

A first method of assisted delivery involves covalent conjugation of lipophilic groups (e.g., acyl or cholesteryl groups) to the 2', 3'-terminus of the molecule. For example, the 2', 5'-cordycepin trimer core may be synthesized and purified with palmitoyl (Formula III) or cholesterylformyl (Formula IV) ester linkages at the 2'-terminal hydroxyl group:

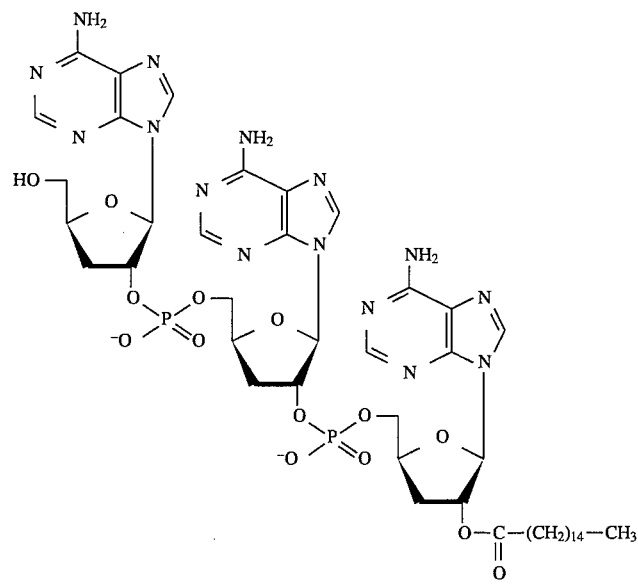
III
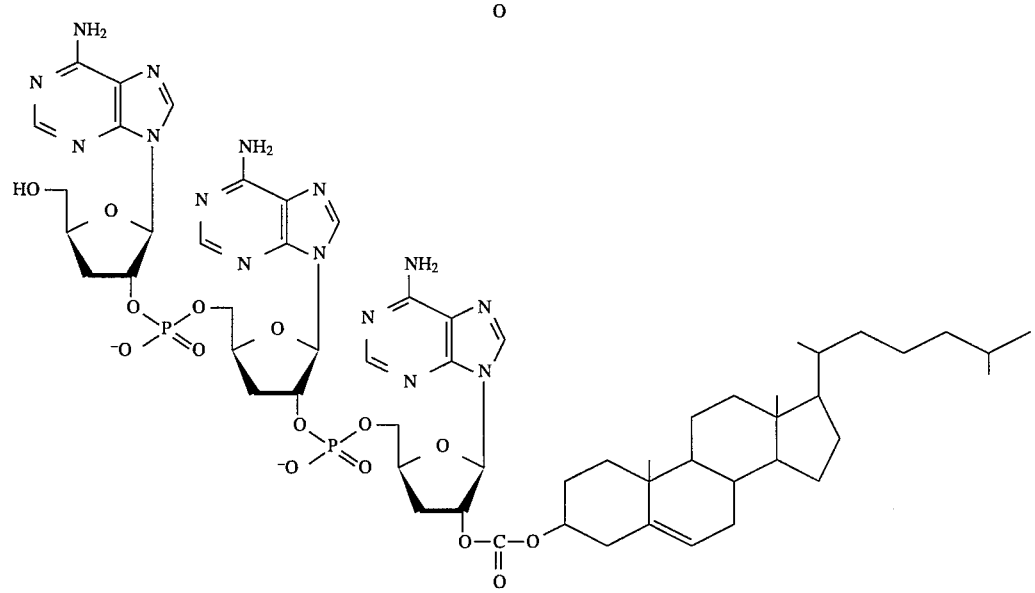
IV
These esterified compounds have been found to inhibit HIV-1 replication in HIV-1 infected H9 cells in culture.

2-5A-analog cholesterol conjugates may be synthesized by reacting a conjugating compound of Formula V

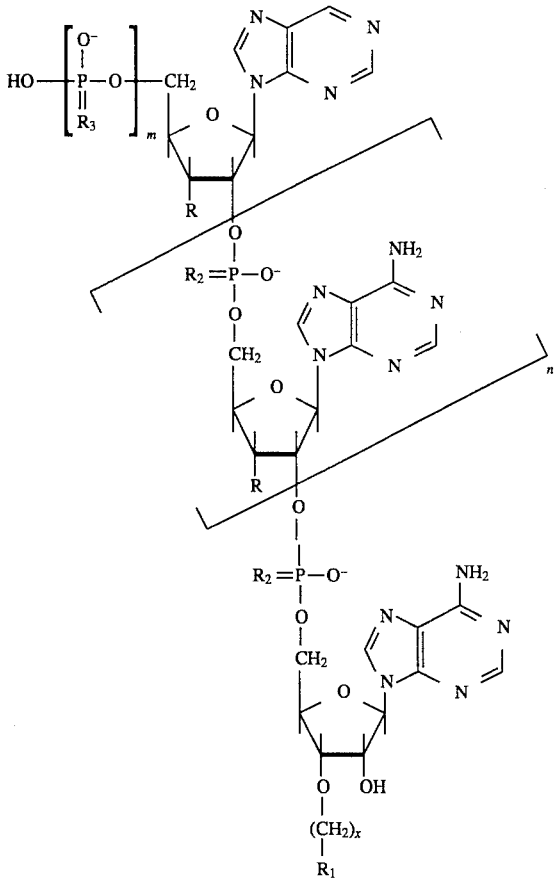

wherein
m is 0, 1, 2 or 3
n is an integer from 1 to 8,
R is independently selected from the group consisting of hydrogen and hydroxyl,
$R_1$ is COOH or $NH_2$, and
$R_2$ is independently sulfur or oxygen
$R_3$ is independently sulfur or oxygen, and
x is an integer from 1 to 17
with chlotesterylchloroformate in the presence of dimethylaminopyridine DMAP) and dichloromethane. Purification is accomplished by column chromatography.

Preferably, not all R groups are hydroxyl, that is, at least one R is hydrogen. Preferably, n is 1 to 3, most preferably 1 or 2. The $R_2$ of the 5'-terminal phosphonyl group is preferably sulfur. Finally, the value of X is preferably from 1 to 8, most preferably 1 to 4. The conjugating 2-5A derivative according to Formula V may be prepared by functionalizing an appropriate 5'-phosphonylated 2', 5'-oligoadenylate, 2', 5'-oligocordycepin or mixed 2', 5'-oligo(adenylate/cordycepin) oligomer, such as may be prepared from either U.S. Pat. No. 4,464,359 or 4,859,768. The oligomer is functionalized by coupling the 2'-terminal nucleotide thereof to an alkyl linker —$(CH_2)_x$—$R_1$ wherein X and R, are defined above.

It should be appreciated that, in addition to oligomers containing phosphodiester internucleotide linkages, the conjugating 2-5A derivative of Formula V may be prepared by attaching the alkyl linker to the 2'-terminal nucleotide of a 2', 5'-phosphorothioate oligonucleotide The preparation of the 2', 5'-phosphorothioates, including fully resolved enantiomers thereof (the phosphorothioates are optically active), is disclosed in U.S. Pat. No. 4,924,624. It may be appreciated that by following the combined synthetic techniques of U.S. Pat. Nos. 4,924,624 and 4,859,768, that a mixed 2', 5'-(phosphodiester/-phosphorothioate)-oligoadenylate may be prepared.

In the case where the $R_2$ group of all internucleotide bonds of the molecule comprise oxygen, i.e., the linkages comprise phosphodiester bonds, the 5'-monophosphates are readily prepared by reacting the corresponding unphosphorylated core compound with $POCl_3$. In the case wherein at least one internucleotide linkage comprises a phosphorothioate bond, i.e., $R_2$=sulfur, such treatment would result in the elimination of sulfur from the phosphorothioate internucleotide linkage, and the formation of a 2', 5'-oligoadenylate. Thus, the 5'-monophosphates of phosphorothioate bond-containing core oligomers must be prepared from the corresponding fully protected core oligomer from which the monomethoxytrityl blocking groups on the 5'-terminal nucleotide has been removed. The procedure is described in detail in U.S. Pat. No. 4,924,624, columns 26 through 31 thereof.

2-5-derivative/acyl conjugates may be synthesized by reacting the conjugating compound with acyl chloride, according to standard techniques. Alternatively, the 2', 5'-oligomer may be synthesized directly with an acyl group or cholesteryl formyl group esterified to the 2'-terminal hydroxyl group. One such method is illustrated by but not limited to the preparation of the cholesterol conjugated and acylated cordycepin trimer compounds comprising compounds 12 and 13 of Scheme 1.

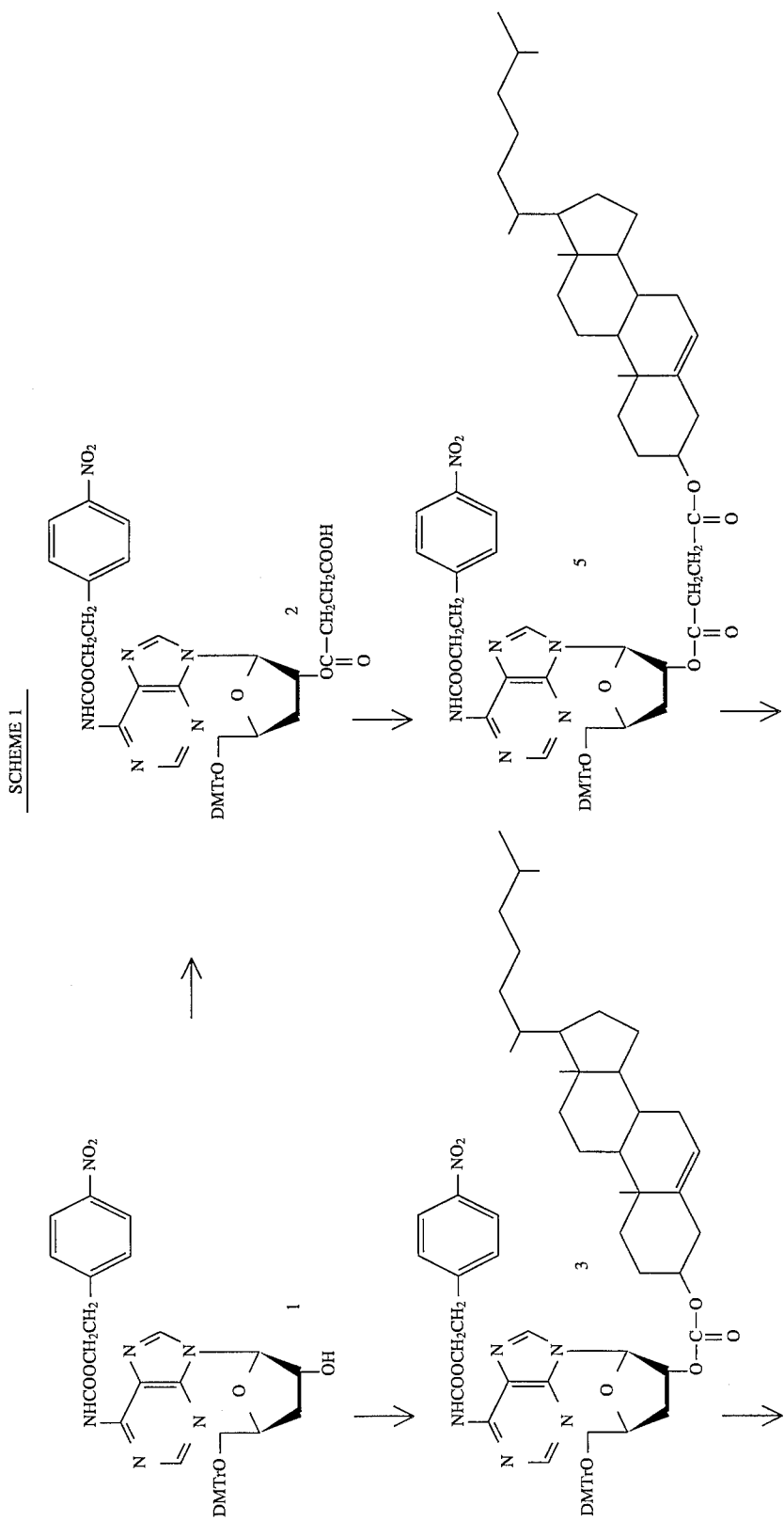

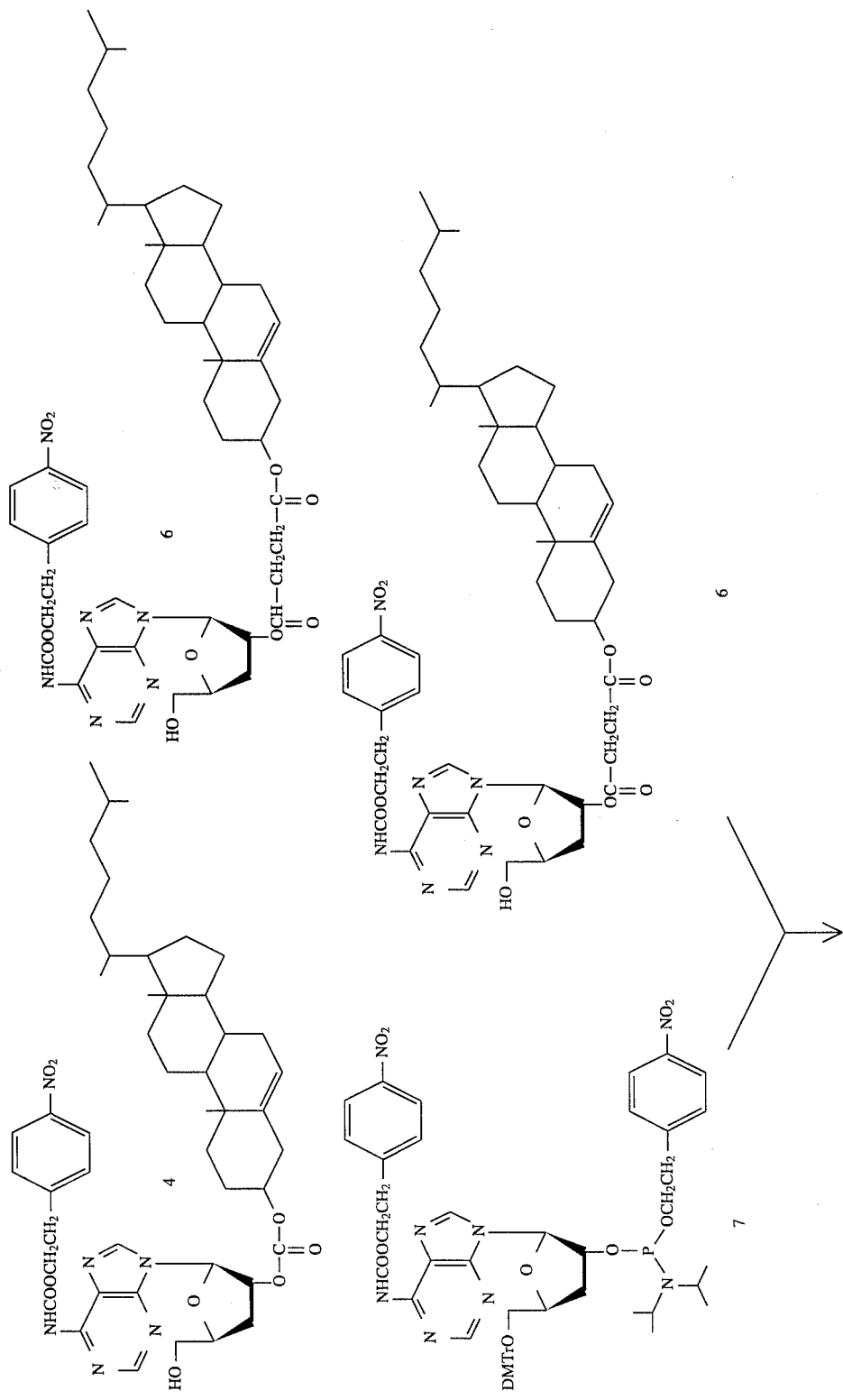

-continued
SCHEME 1
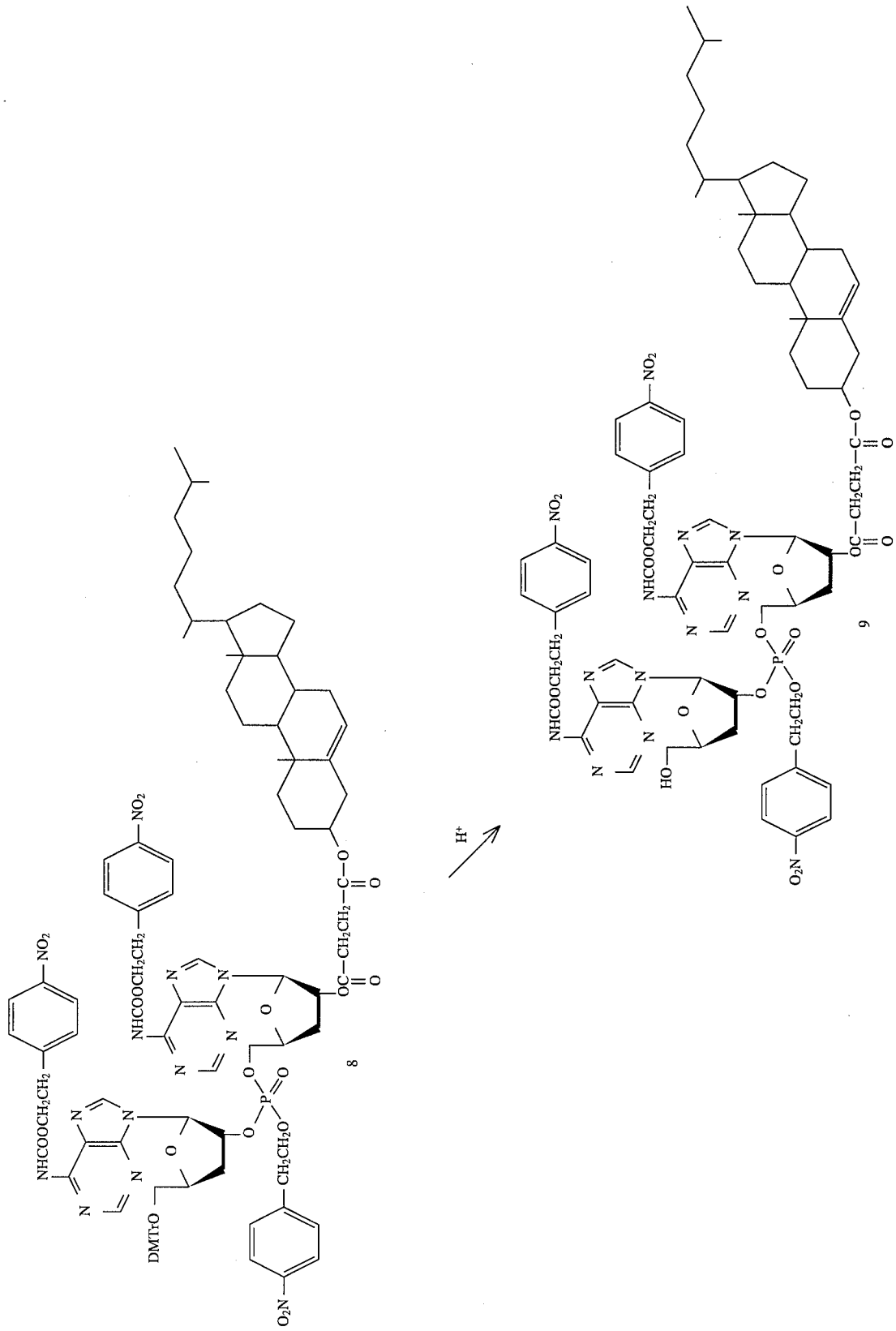

-continued
SCHEME 1
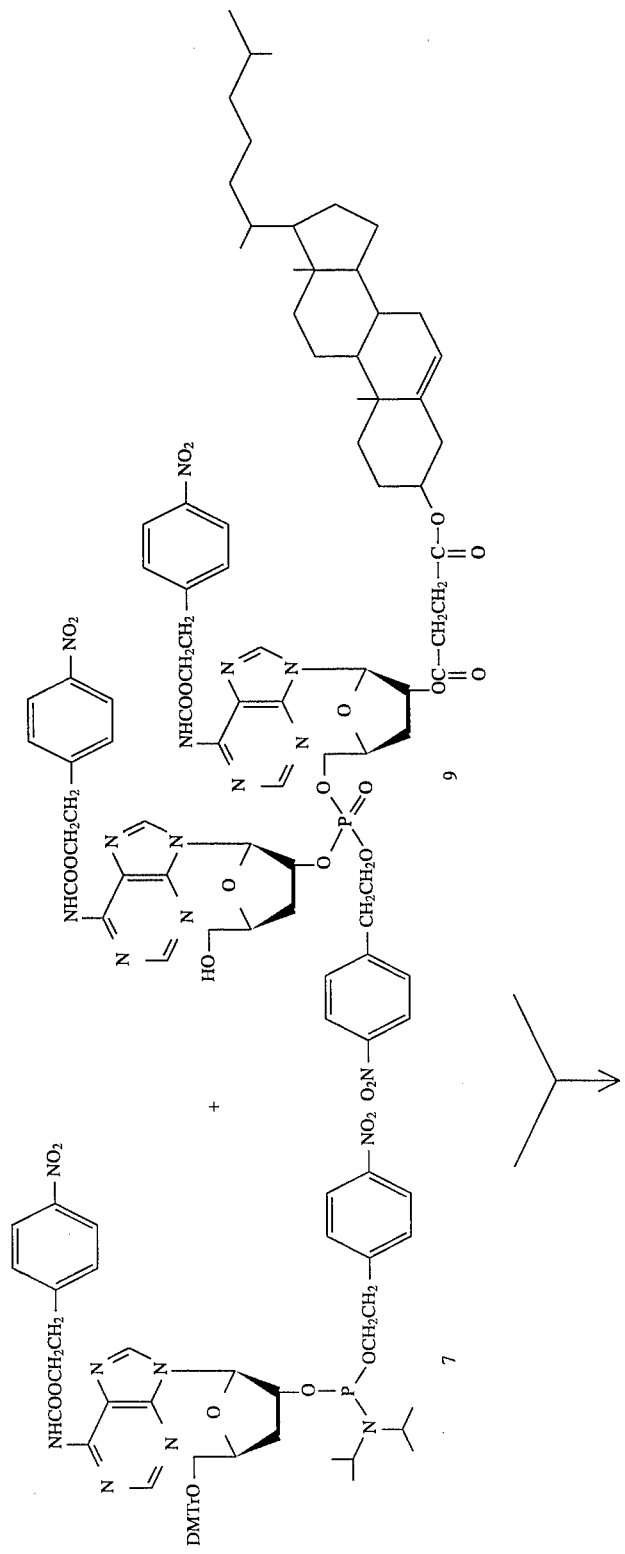

-continued
SCHEME 1
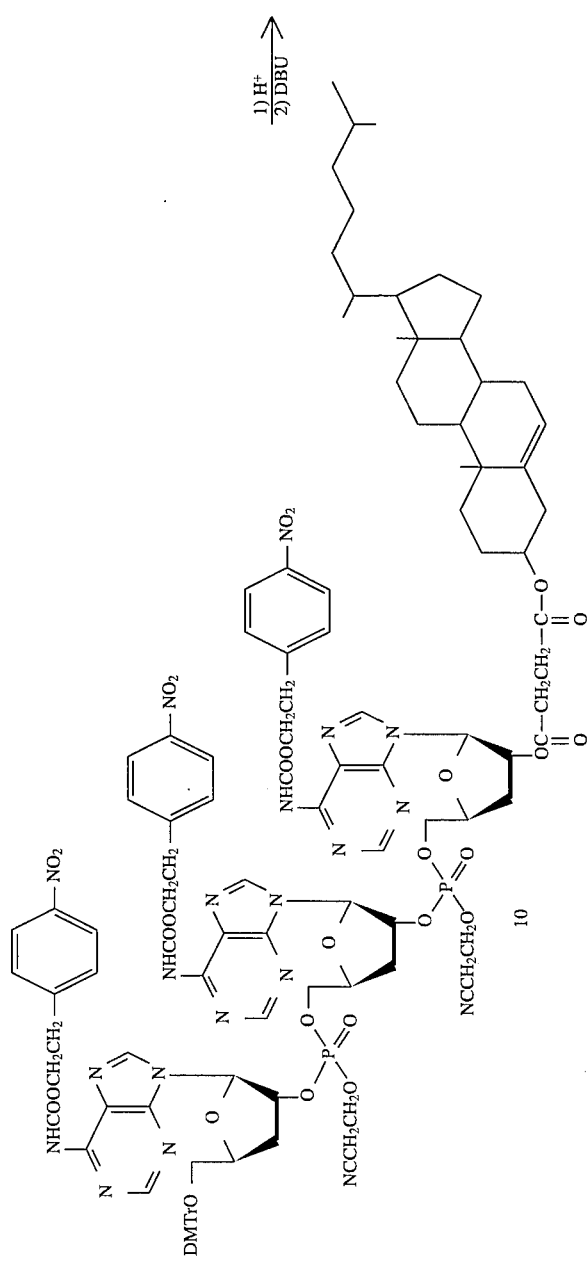

-continued
SCHEME 1
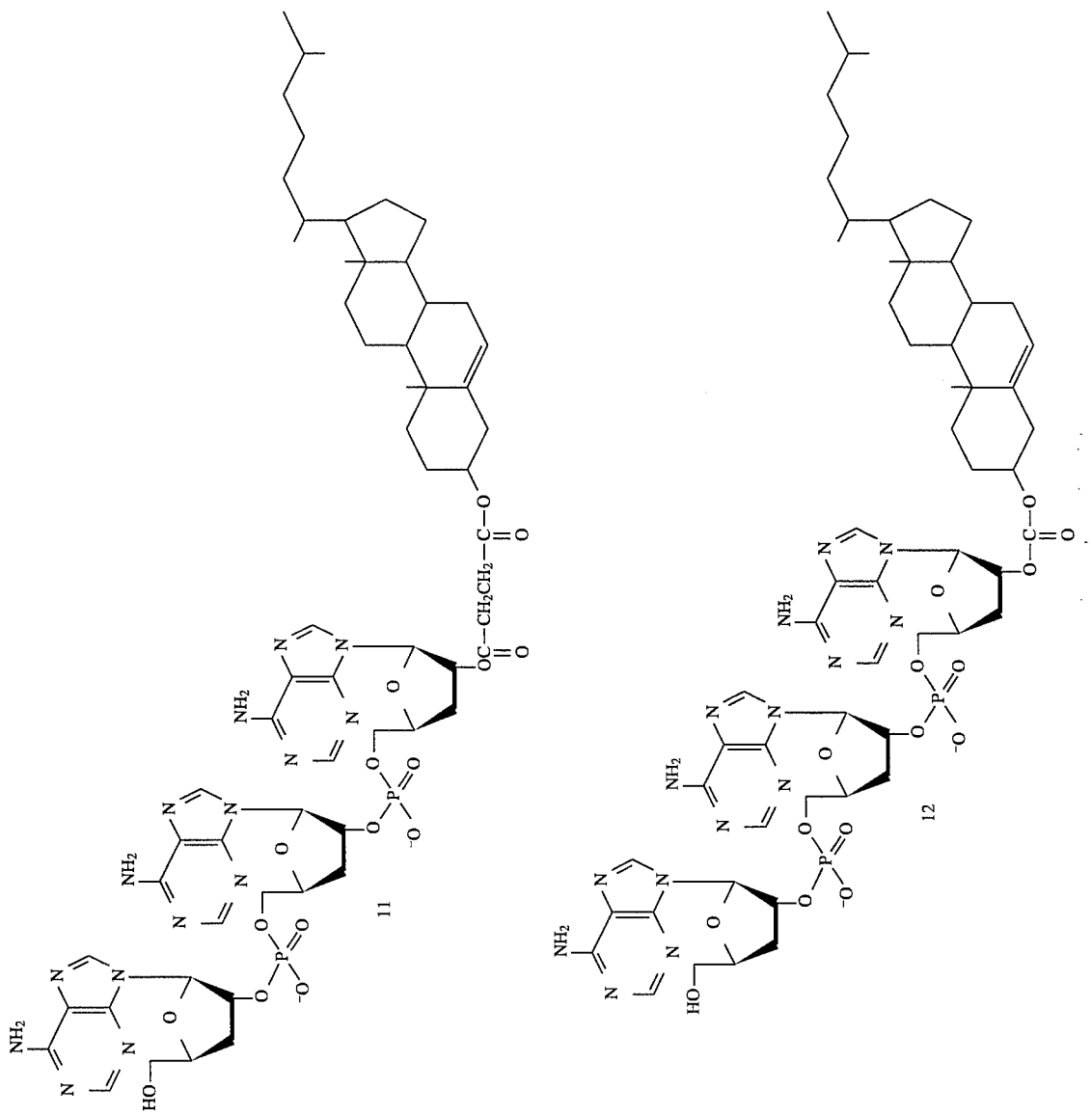

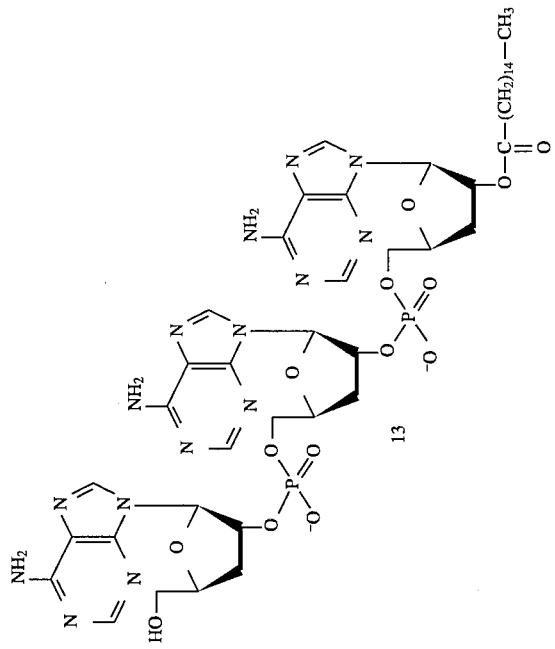
-continued
SCHEME 1

According to Scheme 1, a multistep chemical synthesis starts from 5'-O-dimethoxytrityl-N$^6$-p-nitrophenylethoxy-carbon-yl-cordycepin (1) and the corresponding 2'-O-succinate derivative (2). Compound 1 is reacted with colesteryl chloroformate to the carbonate 3 which is used as the 2'-terminal building block after detritylation to 4. The succinate 2 is condensed with cholesterol to the ester 5, and detritylation leads to compound 6.

The synthetic route to the trimer conjugates is illustrated in Scheme 2 by one example starting from compound 6. This cordycepin derivative is first reacted with the fully protected phosphoramidite 7 to give in excellent yield with the dimer 8. Detritylation at the 5'- end forms 9 and subsequent condensation with a second molecule of 7 gives the fully protected trimer 10. The latter is sequentially treated with acid to cleave the dimethoxytrityl group and by DBU to cleave the p-nitrophenylethoxycarbonyl groups simultaneously, to afford the free cordycepin trimer conjugate 11. The advantage of this approach can be seen from the fact that the ester function between cholesterol and the succinate spacer does survive all the chemical manipulations.

In an entirely analogous manner the cholesterylcarbonate 4 is reacted according to the same sequence of steps to prepare the cordycepine trimer conjugate 12.

Also in an entirely analogous manner, the cordycepin trimer conjugate 13, which carries an acyl residue at the 2'-terminal end of the oligonucleotide, is prepared.

Lipophilic conjugates according to the present invention have the potential to enter the cell by diffusion, owing to their lipophilic nature. They may be introduced into intact cells with substantially the same biological activity as authentic 2-5A. Once inside the cell, the conjugates are hydrolyzed and release the 2-5A derivative.

2', 5'-Oligoadenylate Vitamin Conjugates

A second method of assisted oligonucleotide delivery involves covalent conjugation of 2-5A derivatives to water-soluble vitamins such as biotin, folic acid, riboflavin or vitamin $B_{12}$. Covalent conjugation of 2-5A derivatives to water-soluble vitamins provides a method for co-delivery of active molecules into intact cells by exploiting receptor-mediated endocytosis with retention of essentially full biological activity.

Figure 2A:
FIG. 2A is a phase-contrast micrograph of H9 cells incubated for 5 hours with fluorescein-bovine serum albumin (BSA) covalently conjugated to folate (25 µg/ml) in folate-deficient medium.
Figure 2B:
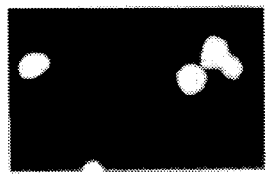
FIG. 2B is a fluorescent micrograph of the same H9 cells shown in FIG. 2A.
Figure 2C:
FIG. 2C is a phase-contrast micrograph of H9 cells incubated for 5 hours with fluorcscein-BSA not conjugated to folate.
Figure 2D:
FIG. 2D is a fluorescent micrograph of the same H9 cells shown in FIG. 2C.

As a mode for demonstrating this principle, we have undertaken internalization of fluorescein-bovine serum albumin (BSA) covalently conjugated to folate in H9 cells in culture (FIGS. 2A and 2B). In control experiments, H9 cells incubated for 5 hours with fluorescein-BSA, but not conjugated to folate, were not taken up (FIGS. 2C and 2D). These results demonstrate the presence of folate receptors on H9 cells, which receptors may be used for targeted delivery of 2-5A derivatives. The folate receptors are able to bind to the folate-conjugated molecule and undergo uptake into 80% of the cells in 5 hours.

2-5A derivatives can be covalently conjugated to water-soluble vitamins to facilitate delivery of the polar 2-5A molecule into intact cells without membrane damage. The water-soluble vitamins are covalently conjugated to the 2', 3'-terminus of the 2-5A molecule to exploit receptor-mediated endocytosis for uptake into intact cells. Nondestructive delivery of polar molecules covalently conjugated to biotin, folic acid, riboflavin and vitamin $B_{12}$ into the cytoplasm and subsequent efficient uptake via receptor-mediated endocytosis has been well demonstrated. In this way, membrane damage arising from other established methods (such as microinjection, electroporation, sonication, detergent permeabilization) can be avoided by employing the natural vitamin endocytosis pathway to accomplish uptake. Vitamin uptake occurs in all dividing cells at reasonable rates. Based on the known efficiency of uptake of vitamin conjugates, it is believed that an intracellular concentration of a 2-5A/folic acid conjugate of about $10^{-6}$M can be achieved; these concentrations are sufficient to activate RNase L and inhibit HIV-1 RT. Similar intracellular concentrations are expected with 2-5A/biotin and the 2-5A/vitamin $B_{12}$ conjugates on the basis of the similar numbers of folate, biotin and vitamin $B_{12}$ receptors.

2-5A Vitamin $B_{12}$ Conjugate

A vitamin $B_{12}$ covalent conjugation of 2-5A or a bioactive 2-5A derivative is prepared by first converting vitamin $B_{12}$ to the mono-acid derivative thereof by mild acid hydrolysis (0.4M HCl, 72 hours at room temperature). A 2-5A conjugating compound, such as a compound according to Formula V ($R_1=NH_2$), is reacted with the carboxyl group of vitamin $B_{12}$ using an appropriate coupling agent such as 1-ethyl-3-(dimethyl-amino-propyl)-carbodiimide HCl (EDAC). The 2-5A/vitamin $B_{12}$ conjugate is purified by either chromatography on Sephadex G-25 or reverse phase HPLC. Characterization is based on the reported molar extinction coefficients for 2-5A and vitamin $B_{12}$.

2-5A/Folic Acid Conjugate

The 2-5A/folic acid conjugate is synthesized by reacting a conjugating compound, such as a compound according to Formula V ($R_1=NH_2$), with a suitable coupling reagent such as EDAC, followed by purification using either column chromatography, thin layer chromatography or HPLC.

2-5A/Biotin Conjugate

Biotinylated 2-5A conjugate may be synthesized by reacting commercially available N-hydroxysuccidimidyl biotin with a Formula V compound ($R_1=NH_2$), followed by purification as described for the 2-5A/folic acid conjugate.

Preparation of 2', 5'-Cordycepin Analogs Containing 3'-Terminal Acyclic Nucleoside Trimer "core" cordycepin analogs according to Formula I, i.e., compounds wherein m is 0 and n is 1 may be prepared according to Scheme 2, wherein "bz" is benzoyl, "MeOTr" is monomethoxytrityl, "npe" is 2-(4-nitrophenyl)ethyl and "npeoc" is [2-(4-nitrophenyl)ethoxy]carbonyl. For illustration purposes, the compounds are prepared as ammonium salts, it being understood that the invention is not so limited. The Scheme is exemplified by the preparation of four compounds, 18, 19, 20 and 21.

Scheme 2

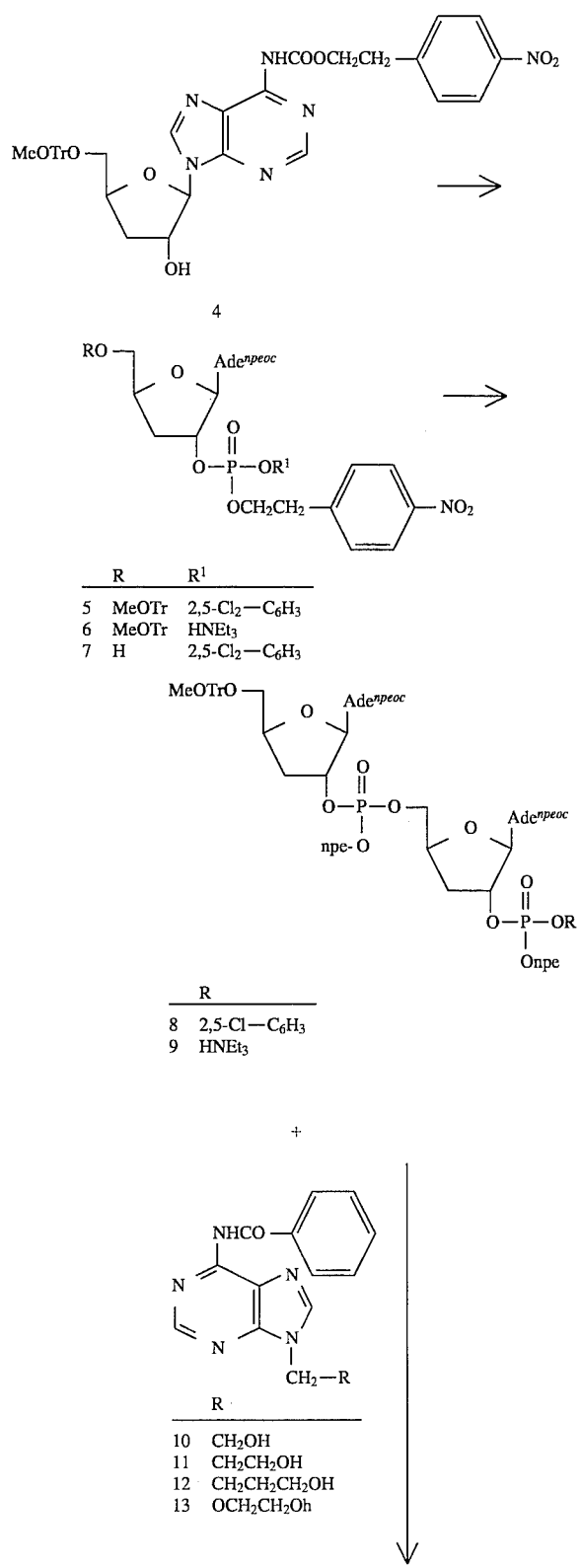

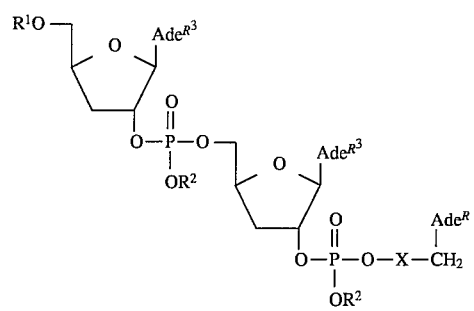

| | R | R¹ | R² | R³ | X |
|---|---|---|---|---|---|
| 14 | bz | MeOTr | npe | npeoc | CH₂ |
| 15 | bz | MeOTr | npe | npeoc | CH₂CH₂ |
| 16 | bz | MeOTr | npe | npeoc | CH₂CH₂CH₂ |
| 17 | bz | MeOTr | npe | npeoc | CH₂CH₂O |
| 18 | H | H | NH₄ | H | CH₂ |
| 19 | H | H | NH₄ | H | CH₂CH₂ |
| 20 | H | H | NH₄ | H | CH₂CH₂CH₂ |
| 21 | H | H | NH₄ | H | CH₂CH₂O | bz = benzoyl
MeOTr = monomethoxytrityl
npe = 2-(4-nitrophenyl)ethyl
npeoc = [2-(4-nitrophenyl)ethoxy]carbonyl The dinucleotide monophosphodiester 9 was prepared from 3'-deoxy-5'-O-(monomethoxytrityl)-N$^6$-[2-(4-nitrophenyl)-ethoxycarbonyl]adenosine (4) according to the method of Charubala et al., *Helv. Chim. Acta* 70, 2028 (1987). Compound 4 which may be prepared according to Charubala et al., was taken and converted into the 2'-phosphotriester 5 with a 2,5-dichlorophenyl and a 2-(4-nitrophenyl)ethyl group at the phosphate function (Scheme 1) according to the method of said Charubala et al. reference. From 5, the 2,5-dichlorophenyl group was cleaved off with 4-nitrobenzaldehyde oxime to give diester 6. On the other hand, the 5'-O-monomethoxytrityl group was removed by acid to give the 5'-hydroxytriester 7. These two building blocks 6 and 7 were condensed in presence of 2,4,6-triisopropylbenzenesulfonyl chloride and 1-methyl-1H-imidazole to yield in 88%, after purification and drying, the dimeric phosphotriester 8. Again, the 2,5-dichlorophenyl group from this dimer block was cleaved off by the oximate method to give the corresponding dinucleotide monophosphodiester 9.

For the syntheses of trimers 14–17, the above dimeric phosphodiester 9 was condensed with the suitably blocked appropriate acyclic nucleosides 10–13 in presence of 2,4,6-triisopropylbenzenesulfonyl chloride and 1-methyl-1H-imidazole in yields of 70–75%. Acyclic nucleosides 10–13 may be prepared according to the procedure of Tychinskaya et al., *Bioorg. Khim (USSP)* 5, 1059 (1979) and Mikhailov et al., *Izv. Akad. Nauk. Ser. Khim.* 2582 (1974). Dimer diester 9 (1 mmol) and the appropriate acyclic nucleoside analog 10–13 (0.75 mmol) were coevaporated with dry pyridine (5×10 ml), and finally dissolved in pyridine (10 ml). Then 0.46 ml (6 mmol) of 1-methyl-1H-imidazole and 0.606 g (2 mmol) of 2,4,6-triisopropylbenzenesulfonyl chloride were added successively. The mixture was stirred at room temperatures for 20 hours, then diluted with CHCl₃ (100 ml), and washed with H₂O(2×50 ml). The organic phase was dried and evaporated, and after coevaporation with toluene (3×20 ml), the residue was purified by CC (silica gel, 10×2.5 cm, CHCl₃/MeOH 100:1): 14–17 as colorless foams in 85–90% yield. Accordingly, to a solution of protected trimer 15–18 (0.028 g; 15 μmol) was added 0.5M DBU in dry pyridine (5 ml). The mixture was stirred at room temperature for 20 hours, neutralized with 1M AcOH in pyridine (2.5 ml), and evaporated. The residue was stirred with concentrated $NH_3$ (15 ml) and after stirring for 48 hours, the solvent was removed in vacuo and the residue detritylated by treatment with 80% AcOH/$H_2O$ (4 ml) at room temperature for 24 hours. After evaporation, the residue was coevaporated several times with $H_2O$, taken up in $H_2O$ and applied onto a DEAE A-25 Sephadex® column (60×1 cm) and eluted with a linear gradient 0.001–0.3M ($Et_3NH$) and $HCO_3$ (TBK) buffer (pH 7.5). The product fractions were evaporated and coevaporated several times with $H_2O$ and further purified by paper chromatography (i-PrOH/conc. $NH_3H_2O$ 6:1:3). The product band was cut out and eluted with $H_2O$ and lyophilized to give 3'-deoxyadenylyl-(2'-5')-3'-deoxyadenylyl-(2'-2')-9-(2'-hydroxyethyl)adenine (diammonium salt; 19), 3'-deoxyadenylyl-(2'- 5')-3'-deoxyadenylyl-(2'-3')-9-(3'-hydroxypropyl)adenine(diammonium salt; 19), 3'-deoxyadenylyl-(2'-5')-3'-deoxyadenylyl(2'-4')-9-(4'-hydroxybutyl)adenine (diammonium salt; 20), and 3'-deoxyadenylyl-(2'-5')-3-deoxyadenylyl-(2'-2")-9-[(2"-hydroxyethoxy)methyl]adenine diammonium salt; 21, respectively, as colorless powders in 75–85% yield. The purity of all products was checked by TLC, UV, and ¹H-NMR spectra.

All trimers were deblocked sequentially, using 0.5M DBU (1,8-diazabicyclo[5.4.0]undec-7-ene) in dry pyridine for 20 hours at room temperature to cleave the 2-(4-nitrophenyl)-ethyl groups, $NH_3$ in dioxane to remove the benzoyl groups, and finally acid treatment to deblock the 5'-O-monomethoxytrityl group yielding the corresponding fully deblocked trimers 18–21, which were purified by DEAE sephadex column chromatographyand paper chromatography. The trimers were characterized by TLC, UV, HPLC, and ¹H-NMR spectra (data not shown).

Tetramers (C-C-C-ether-A) may be prepared by substituting for the dinucleotide monophosphodiester 9 in Scheme 2 the corresponding protected trinucleotide 9a which is condensed with the suitably blocked appropriate acyclic nucleoside, as above. Similarly, it should be clear that higher oligomers of the present 3'-acyclic cordycepin oligomers may be prepared by selecting the appropriate higher oligonucleotide for condensation with the acyclic nucleoside.

The 5'-monophosphates of the unphosphorylated core molecules may be prepared from the fully blocked trimers, e.g., 14–17 by detritylation with acid treatment, followed by reaction with di-p-nitrophenylethylphosphoryl chloride. Further deblocking and chromatography results in isolation of the 5'-monophosphate oligomers. The 5'-monophosphorylation procedure may be carried out according to the method of Example 6 of U.S. Pat. No. 4,859,768.

The 5'-diphosphates and 5'-triphosphates of the core molecules may be prepared according to the procedure of the aforesaid patent. Briefly, they may be prepared by adding 0.5 mM of tributylammonium pyrophosphate dissolved in 5 ml of dimethylformamide to 0.1 mM of monophoosphorylated core as the anhydrous tributylammonium salt in 1 ml of dimethylformamide and 0.5 mM of 1,1'-carbonyldiimidazole. After 20 hours at room temperature, the reactants are treated with 5 ml of methanol, evaporated to dryness and chromatographed on a 2×20 cm DEAE cellulose column. The 5'-di and triphosphates are isolated following a linear gradient (0–0.4M in 3 1 at pH 7.5) of triethylammoniumbicarbonate, according to the method of Hoard, et al., *J. Amer. Chem. Soc.* 87, 1785–1788 (1965). The 5'-diphosphates and 5'-triphosphates may then be purified by DEAE-Sephadex® A25 and Sephadex®.

The 2-5A analogs and conjugates may be administered according to the methods described in U.S. Pat. Nos. 4,924, 624, 4,859,768 and patent application Ser. No. 613,848, in the dosages recommended therein. In addition, 2-5A derivatives and conjugates may be administered via microscopic nanometer-size polystyrene carriers which dissolve in the bloodstream to release the active drug. Other suitable carriers are discussed in the aforementioned patent documents, the entire disclosures of which are incorporated herein by reference.

All references with respect to synthetic, preparative and analytic procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A compound according to the formula

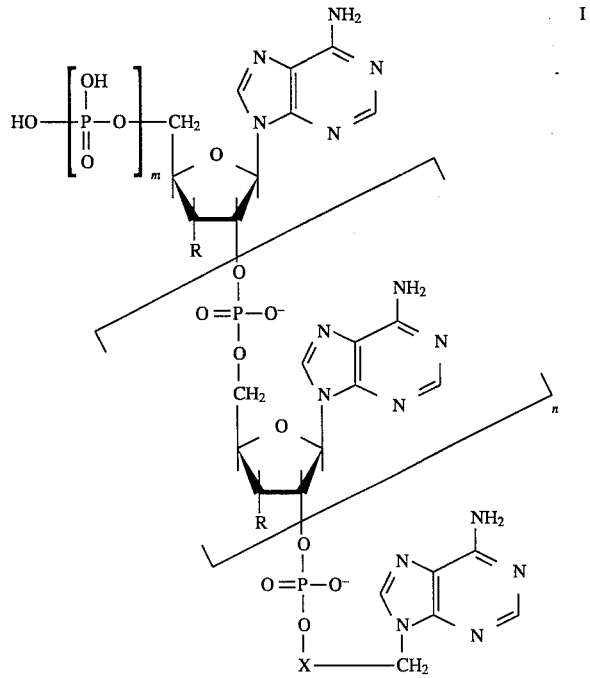

wherein n is a whole positive integer from 1 to 8, m is 0, 1, 2 or 3,

R is hydrogen,

X is selected from the group consisting of C1 to C6 alkyl and C1 to C6 alkoxy, or a pharmaceutically acceptable salt thereof.

2. A compound according to claim 1 wherein X is selected from the group consisting of C1 to C3 alkyl and C1 to C3 alkoxy.

3. A compound according to claim 1 wherein the compound is selected from the group consisting of 3'-deoxy-aden-ylyl-( 2'-5')-3'-deoxyadenylyl(2'-2')-9-(2'hydroxyethyl)adenine, the 5' mono-, di- and triphosphates thereof and, any pharmaceutically acceptable salts of said compounds.

4. A compound according to claim 1 wherein the compound is selected from the group consisting of 3'-deoxyaden-ylyl-(2', 5')-3'-deoxyadenylyl-(2', 3')-9-(3'-hydroxypropyl)adenine, the 5' mono-, di- and triphosphates thereof and, any pharmaceutically acceptable salts of said compounds.

5. A compound according to claim 1 wherein the compound is selected from the group consisting of 3'-deoxyadenylyl-(2', 5')-3'-deoxyadenylyl-(2', 4')-9-(4'-hydroxybutyl)adenine, the 5' mono-, di- and triphosphates thereof and, any pharmaceutically acceptable salts of said compounds.

6. A compound according to claim 1 wherein the compound is selected from the group consisting of 3'-deoxyaden-ylyl-(2', 5')-3'-deoxyadenylyl-(2', 2')-9-[(2"-hydroxyethoxy)methyl]adenine, the 5' mono-, di- and triphosphates thereof, and any pharmaceutically acceptable salts of said compounds.

7. A pharmaceutical composition comprising a compound according to claim 1 and a pharmaceutical carrier.

8. A conjugate comprising a compound according to the formula

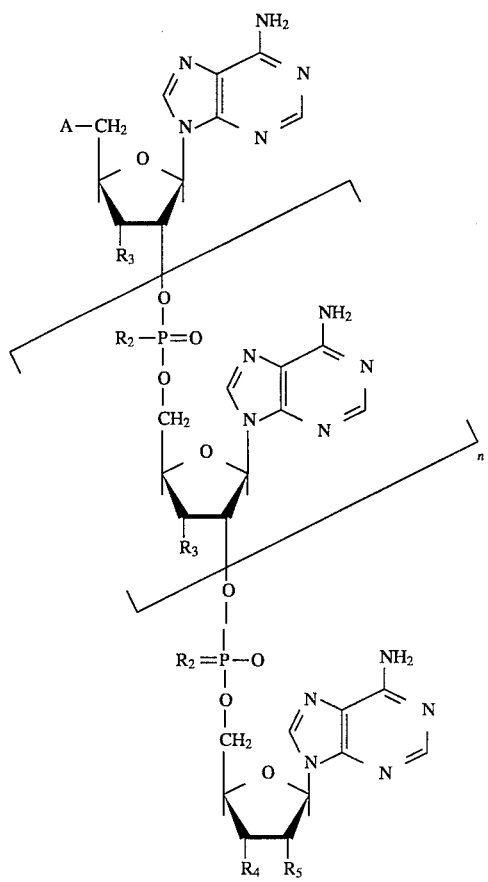

wherein
A is

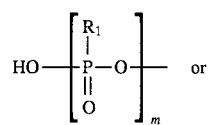  or

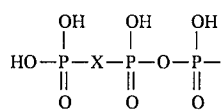

X is $NH_2$ or $CH_2$;

m is zero, 1 2 or 3;

n is an integer from 1 to 8;

each $R_1$ is independently selected from the group consisting of O, S, sulfate, Se, $C_1$ to $C_8$ alkyl and $C_1$ to $C_8$ alkoxy;

each $R_2$ is independently selected from the group consisting of O, S-, sulfate, Se, $C_1$ to $C_8$ alkyl and C1 to $C_8$ alkoxy;

each $R_3$ is independently selected from hydrogen, hydroxyl, amino and $—OSi(CH_3)_2C(CH_3)_3$;

$R_4$ and $R_5$ are independently selected from the group consisting of hydrogen; hydroxyl; amino; $C_1$ to $C_8$ alkyl; $C_1$ to $C_8$ alkoxy; $C_1$ to $C_8$ alkylamino, alkylcarbonyl, alkylcarboxyl and alkylhalide; and $C_1$ to $C_8$ alkoxyamino, alkoxycarbonyl, alkoxycarboxyl and alkoxyhalide; or pharmaceutically acceptable salts thereof, provided the compound is not authentic 2', 5'-oligoadenylate or a salt thereof, said compound being covalently linked through an optional linker to an adduct through a hydroxyl oxygen at the 2'- or 3'-position of the 2'-terminal nucleotide of said compound, which adduct is selected from the group consisting of vitamin $B_{12}$, biotin, folic acid, riboflavin, cholesterol and an acyl group of the formula

wherein x is an integer from 1 to 20.

9. A conjugate according to claim 8 wherein the adduct is vitamin $B_{12}$.

10. A conjugate according to claim 8 wherein the adduct is biotin.

11. A conjugate according to claim 8 wherein the adduct is folic acid.

12. A conjugate according to claim 8 wherein the adduct is an acyl group of the formula

wherein x is an integer from 1 to 20.

13. A conjugate according to claim 8 wherein the adduct is the colesteryl group.

14. A conjugate according to claim 8 wherein
A is

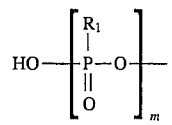

m is zero, 1, 2 or 3, n is an integer from 1 to 8, each $R_3$ and $R_4$ is independently selected from hydrogen and hydroxyl, each $R_2$ is independently selected from $S^-$ and $O^-$, $R_5$ is hydroxy, or a pharmaceutically acceptable salt thereof, which compound is covalently linked through the 2'-position of the 2'-terminal nucleotide thereof to said adduct.

15. A conjugate according to claim 12 wherein the vitamin is selected from the group consisting of $B_{12}$, folic acid and biotin.

16. A conjugate according to claim 12 wherein the adduct is cholesteryl.

17. A conjugate according to claim 12 wherein the adduct is an acyl group of the formula

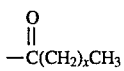

wherein X is an integer from 1 to 20.

18. A conjugate according to claim 17 wherein the adduct is palmitoyl.

19. A method for inhibiting vital infection comprising administering to a mammal in need of such treatment an effective amount of a conjugate according to claim 8.

20. A method for treating viral infection comprising administering to a mammal in need of such treatment an effective amount of a compound according to claim 1.

21. A method for treating viral infection comprising administering to a mammal in need of such treatment an effective amount of a compound according to claim 2.

22. A method of antiviral treatment comprising administering to a mammal an effective amount of a compound according to the formula

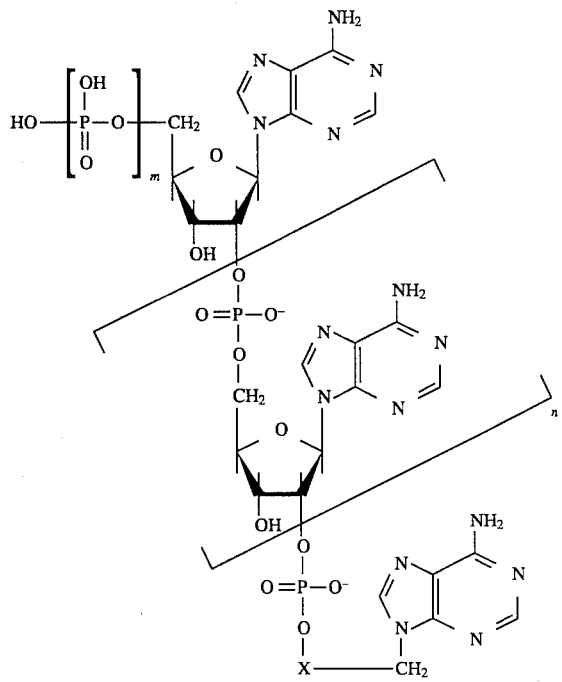

wherein n is a whole positive integer from 1 to 8, m is 0, 1, 2 or 3,

X is selected from the group consisting of C1 to C6 alkyl and C1 to C6 alkoxy, or a pharmaceutically acceptable salt thereof.

23. A method according to claim 22 wherein X is selected from the group consisting of C1 to C3 alkyl and C1 to C3 alkoxy.

24. A method according to claim 23 wherein the compound is selected from the group consisting of adenylyl-(2'- 5')-adenylyl(2'- 2')-9-(2'-hydroxyethyl)adenine, the 5'mono-, di- and triphosphates thereof, and any pharmaceutically acceptable salts of said compounds.

25. A method according to claim 22 wherein the compound is selected from the group consisting of adenylyl-(2', 5')-adenylyl-(2', 3')-9-(3'-hydroxypropyl)adenine, the 5'mono-, di- and triphosphates thereof, and any pharmaceutically acceptable salts of said compounds.

26. A method according to claim 22 wherein the compound is selected from the group consisting of adenylyl-(2', 5')-adenylyl-(2', 4')-9-(4'-hydroxybutyl)adenine, the 5'mono-, di- and triphosphates thereof, any pharmaceutically acceptable salts of said compounds.

27. A method according to claim 22 wherein the compound is selected from the group consisting of adenylyl-(2', 5')-adenylyl-(2', 2')-9-[(2''-hydroxethoxy)methyl]adenine, the 5'mono-, di- and triphosphates thereof, and any pharmaceutically acceptable salts of said compounds.

28. A method according to claim 27 wherein the compound is adenylyl-(2', 5')-adenylyl-(2', 2')-9-[(2''-hydroxethoxy)-methyl]adenine, or a pharmaceutically acceptable salt thereof.

29. A pharmaceutical composition comprising a compound according to the formula

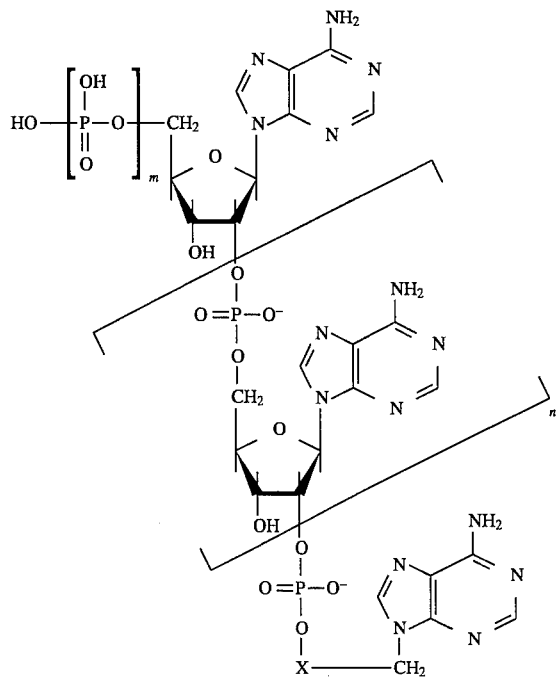

wherein n is a whole positive integer from 1 to 8, m is 0, 1, 2 or 3,

X is selected from the group consisting of C1 to C6 alkyl and C1 to C6 alkoxy, or a pharmaceutically acceptable salt thereof, and a pharmaceutical carrier.

30. A composition according to claim 29 wherein the compound is selected from the group consisting of adenylyl-(2', 5')-adenylyl-(2', 2')-9-[(2''-hydroxethoxy)methyl]adenine, the 5'mono-, di-and triphosphates thereof, and any pharmaceutically acceptable salt of said compounds.

31. A composition according to claim 30 wherein the compound is adenylyl-(2', 5')-adenylyl-(2', 2')-9-[(2''-hydroxethoxy)methyl]adenine, or a pharmaceutically acceptable salt thereof.

* * * * *